US010233232B2

(12) United States Patent
Hansman et al.

(10) Patent No.: US 10,233,232 B2
(45) Date of Patent: Mar. 19, 2019

(54) NOROVIRUS ANTIBODIES

(71) Applicants: Deutsches Krebsforschungszentrum, Heidelberg (DE); Ruprecht-Karls-Universität Heidelberg, Heidelberg (DE)

(72) Inventors: Grant Hansman, Heidelberg (DE); Anna Koromyslova, Dossenheim (DE)

(73) Assignees: Deutsches Krebsforschungszentrum, Heidelberg (DE); Ruprecht-Karls-Universität Heidelberg, Heidelberg (DE)

(*) Notice: Subject to any disclaimer, the term of this patent is extended or adjusted under 35 U.S.C. 154(b) by 0 days.

(21) Appl. No.: 15/516,888

(22) PCT Filed: Oct. 14, 2015

(86) PCT No.: PCT/EP2015/073781
§ 371 (c)(1),
(2) Date: Apr. 4, 2017

(87) PCT Pub. No.: WO2016/059113
PCT Pub. Date: Apr. 21, 2016

(65) Prior Publication Data
US 2017/0247434 A1    Aug. 31, 2017

(30) Foreign Application Priority Data
Oct. 14, 2014   (EP) ..................................... 14188878

(51) Int. Cl.
*C07K 16/10*       (2006.01)
*G01N 33/569*      (2006.01)
*C07K 7/06*        (2006.01)
*C07K 7/08*        (2006.01)

(52) U.S. Cl.
CPC ............... *C07K 16/10* (2013.01); *C07K 7/06* (2013.01); *C07K 7/08* (2013.01); *G01N 33/56983* (2013.01); *C07K 2317/22* (2013.01); *C07K 2317/34* (2013.01); *C07K 2317/565* (2013.01); *C07K 2317/569* (2013.01); *C07K 2317/70* (2013.01); *C07K 2317/76* (2013.01); *C07K 2317/92* (2013.01); *G01N 2333/08* (2013.01)

(58) Field of Classification Search
None
See application file for complete search history.

(56) References Cited

U.S. PATENT DOCUMENTS 5,591,828 A    1/1997   Bosslet et al.

FOREIGN PATENT DOCUMENTS

| EP | 0 404 097 A2 | 12/1990 |
|----|--------------|---------|
| EP | 2 757 111 A1 | 7/2014 |
| KR | 20090078137 A | 7/2009 |
| WO | WO 93/01161 | 1/1993 |
| WO | WO 2014/126921 A1 | 8/2014 |

OTHER PUBLICATIONS

Rudikoff et al Proc Natl Acad Sci USA 1982 vol. 79 p. 1979.*
MacCallum et al. J. Mol. Biol. (1996) 262, 732-745.*
Casset et al. (2003) BBRC 307, 198-205.*
Kashmiri et al. Methods. 2005; 36:25-34.*
Tamura et al. Journal of Immunology. 2000; 164:1432-1441.*
Zabetakis et al., PLOS ONE vol. 8, No. 10, e77678, 2013.*
International Search Report and Written Opinion issued in related International Patent Application No. PCT/EP2015/073781, completed Dec. 10, 2015.
International Preliminary Report on Patentability issued in related International Patent Application No. PCT/EP2015/073781, dated Apr. 27, 2017.
Adams, et al., "PHENIX: a comprehensive Python-based system for macromolecular structure solution," Acta Crystallographica Section D, *Biological Crystallography*, D66, pp. 213-221 (2010).
Desmyter et al., "Crystal structure of a camel single-domain VH antibody fragment in complex with lysozyme," *Nature Structural Biology*, vol. 3, pp. 803-881 (Sep. 1996).
Chen, et al., "MolProbity: all-atom structure validation for macromolecular crystallography," *Acta crystallographica*, Section D, *Biological crystallography* 66 , pp. 12-21 (2010).
Emsley, et al., "Features and development of Coot," *Acta Crystallogr D Biol Crystallogr* 66, pp. 486-501 (2010).
Hansman, et al., "Crystal structures of GII.10 and GII.12 norovirus protruding domains in complex with histo-blood group antigens reveal details for a potential site of vulnerability," *Journal of Virology* 85:6687-6701 (Jul. 2011).
Hansman, et al., "Structural basis for broad detection of genogroup II noroviruses by a monoclonal antibody that binds to a site occluded in the viral particle," *Journal of Virology* 86, pp. 3635-3646 (2012).
Hansman, "Genetic and antigenic diversity among noroviruses," J Gen Virol 87:909-919 (2006).

(Continued)

*Primary Examiner* — Shanon A. Foley
*Assistant Examiner* — Myron G Hill
(74) *Attorney, Agent, or Firm* — Foley & Lardner LLP

(57) ABSTRACT

The present invention relates to a binding polypeptide specifically binding to the amino acid sequence W-V-N-$X^1$-F-Y-$X^2$ (SEQ ID NO: 1), wherein $X^1$ represents any amino acid, preferably Q or P, and wherein $X^2$ represents any amino acid, preferably, T or S in a norovirus polypeptide. The present invention further relates to polynucleotide encoding a binding polypeptide of the present invention an to a host cell comprising the same or the polynucleotide of the invention. The present invention further relates to a method of detecting the presence of a norovirus capsid polypeptide in a sample and to kits, devices, and uses making use of the binding peptide of the invention.

10 Claims, 10 Drawing Sheets

Figure 1A:
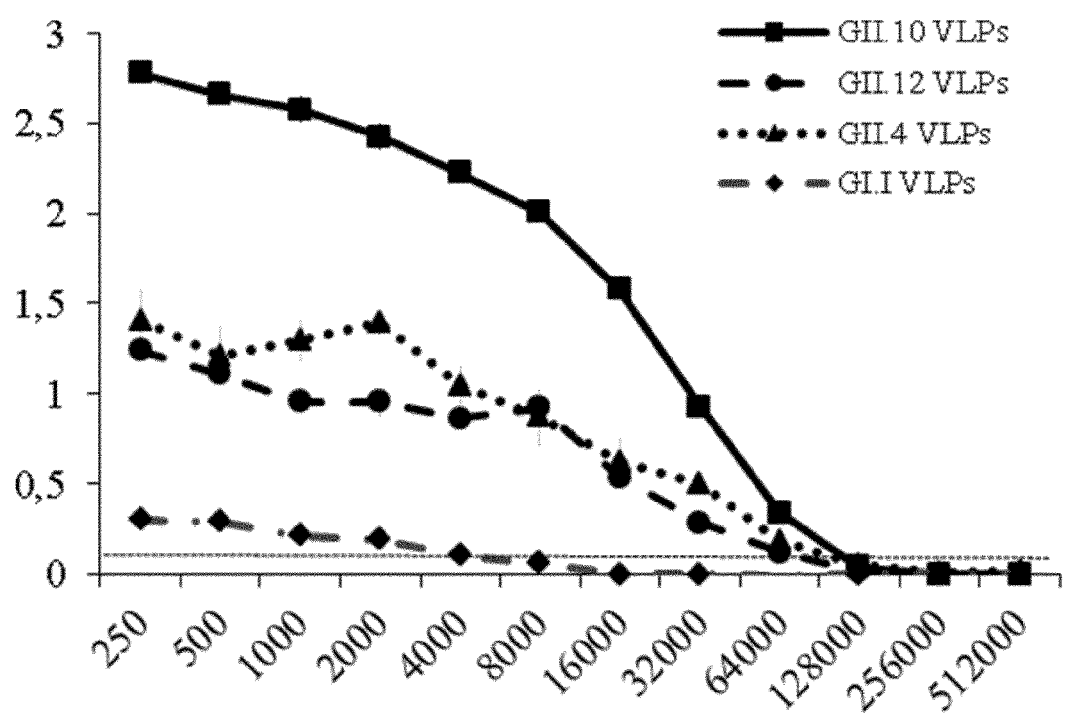

Specification includes a Sequence Listing.

(56) References Cited

OTHER PUBLICATIONS

Hansman, et al., "Detection of norovirus and sapovirus infection among children with gastroenteritis in Ho Chi Minh City, Vietnam," Arch Virol 149:1673-1688 (May 2004).
Hansman, "Development of an antigen ELISA to detect sapovirus in clinical stool specimens," Arch Virol. 151:551-561 (2006).
Higgins et al., "Fast and sensitive multiple sequence alignments on a microcomputer," CABIOS, vol. 5 , No. 2, pp. 151-153 (1989).
Hollinger et al., "Diabodies, Small bivalent and bispecific antibody fragments," PNAS USA 90, pp. 6444-6448 (1993).
Hudson et al., "Engineered Antibodies," Nat. Med., vol. 9, No. 1, pp. 129-134 (Jan. 2003).
Kabsch, "Automatic processing of rotation diffraction data from crystals of initially unknown symmetry and cell constants," J Appl Cryst 26, pp. 795-800 (1993).
Krissinel, et al., "Inference of macromolecular assemblies from crystalline state," Journal of molecular biology, vol. 372, pp. 774-797 (2007).
Kroneman, et al., "Proposal for a unified norovirus nomenclature and genotyping," Arch Virol., vol. 158, pp. 2059-2068 (2013).
McCoy, et al., "Phaser crystallographic software," Journal of Applied Crystallography 40: 658-674 (2007).
Lin, et al., "A comparison of hand washing techniques to remove *Escherichia coli* and caliciviruses under natural or artificial fingernails," J Food Prot 66, pp. 2296-2301 (2003).
Morris, et al., "Stereochemical quality of protein structure coordinates," Proteins 12, pp. 345-364 (1992).
Needleman et al., "A General Method Applicable to the Search for Similarities in the Amino Acid Sequence of Two Proteins," J. Mol. Biol. 48, pp. 443-453 (1970).
Parker, et al., "Identification of Genogroup I and Genogroup II broadly reactive epitopes on the norovirus capsid," Journal of Virology 79, pp. 7402 7409 (2005).
Feng et al., "Progressive Sequence Alignment as a Prerequisite to Correct Phylogenetic Trees," J. Mol. Evolution., vol. 25, pp. 351-360 (1987).
Prasad, et al., "X-ray crystallographic structure of the Norwalk virus capsid," Science 286, pp. 287-290 (1999).
Prasad, "Three-dimensional structure of baculovirus-expressed Norwalk virus capsids," Journal of Virology 68, pp. 5117-5125 (1994).
Shiota, et al., "Characterization of a broadly reactive monoclonal antibody against norovirus genogroups I and II: recognition of a novel conformational epitope," Journal of Virology 81, pp. 12298-12306 (2007).
Smith, et al., "Comparison of Biosequences," Adv. Appl. Math. 2; pp. 482-489 (1981).
Dowdy and Wearden, Statistics for Research, John Wiley & Sons, New York 1983, 15 pages (Book), TOC and Preface provided.
Smith, "Structural studies on antibody recognition and neutralization of viruses," Curr Opin Virol 1, pp. 150-156 (2011).
Tan et al., "Norovirus and its histo-blood group antigen receptors: an answer to a historical puzzle," Trends in Microbiology 13(6), pp. 285-293 (Jun. 2005).
Tian et al., "Porcine gastric mucin binds to recombinant norovirus particles and competitively inhibits their binding to histo-blood group antigens and Caco-2 cells," Lett Appl Microbiol 41(4), pp. 315-320 (2005).
Current Protocols in Molecular Biology, John Wiley & Sons, N.Y., 6.3.1-6.3.6 (1989), 6 pages.
Sano et al., "Norovirus-binding proteins recovered from activated sludge micro-organisms with an affinity to a noroviral capsid peptide," Journal of Applied Microbiology 109(6), pp. 1923-1928 (2010).
Dai et al., "Evaluation of anti-norovirus IgY from egg yolk of chickens immunized with norovirus P particles," Journal of Virological Methods 186(1-2), pp. 126-131 (2012).
Garaicoechea, et al., "Congresses and Scientific Meetings, American Society of Virology Annual Meeting" XP055177898 (2012), 1 page Abstract.
Hussack et al., "Neutralization of Clostridium difficile Toxin A with Single-domain Antibodies Targeting the Cell Receptor Binding Domain," Journal of Biological Chemistry 286(11), pp. 8961-8976 (2011).
Chen et al., "Bioinformatics analysis of the epitope regions for norovirus capsid protein", BMC Bioinformatics, 14(Suppl 4):S5 (2013), 6 pages.

\* cited by examiner

A

DVQLVESGGG LVQPGGSLRL SCAAS<u>GSIFS</u> IYAMGWYRQA
PGKQRELVAS <u>ISSGGGTN</u>YA DSVKGRFTIS GDNAKNTVYL
QMNSLKPEDT AVYYC<u>KREDY SAYAPPSGS</u>R GRGTQVTVSS
GRYPYDVPDY GSGRA

B gatgtgcagc tggtggagtc tgggggaggc ttggtgcagc ctggggggtc
tctgagactc tcctgtgcag cctctggaag catcttcagt atctatgcca
tgggctggta ccgccaggct ccagggaagc agcgcgagtt ggtcgcttct
attagtagtg gtggtggcac aaactatgca gactccgtga agggccgatt
caccatctcc ggagacaacg ccaagaacac ggtgtatctg caaatgaaca
gcctgaaacc tgaggacacg gccgtctatt actgtaaaag agaagactat
agcgcctatg cgcccccgag tggttcccgg ggccggggga cccaggtcac
cgtctcctca caccaccatc accatcacta a

Fig. 3

A  B
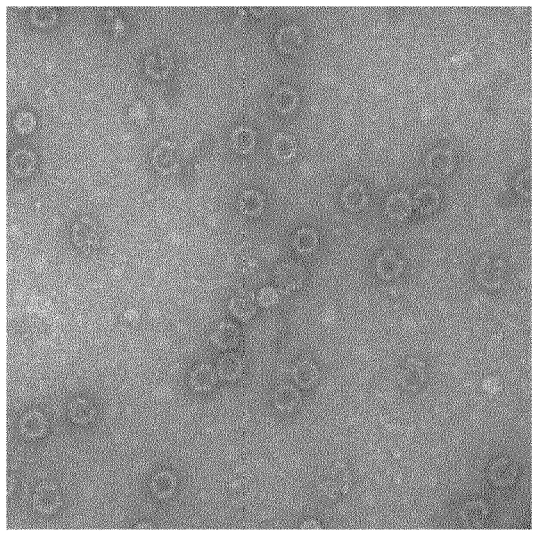 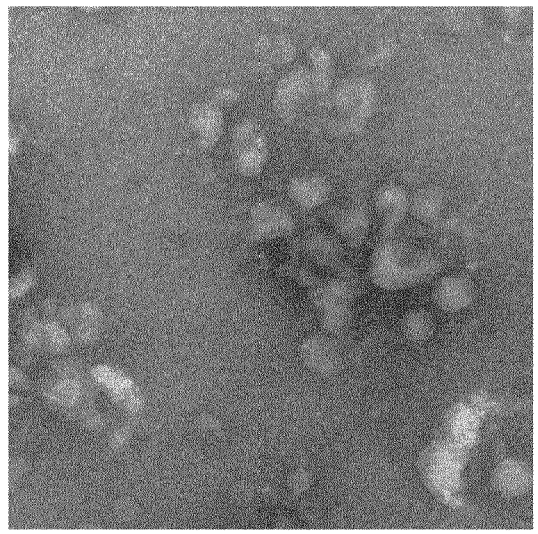
Fig. 5

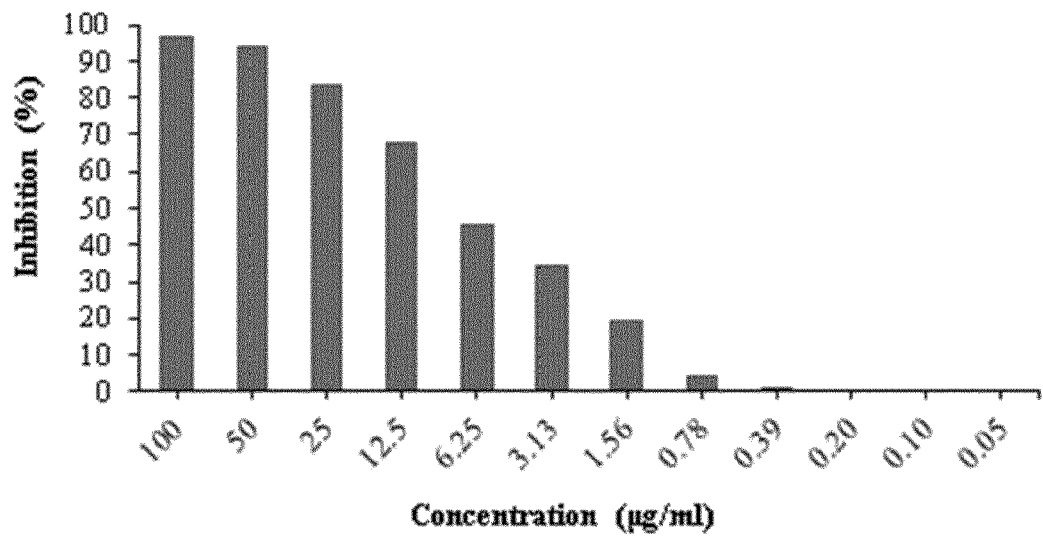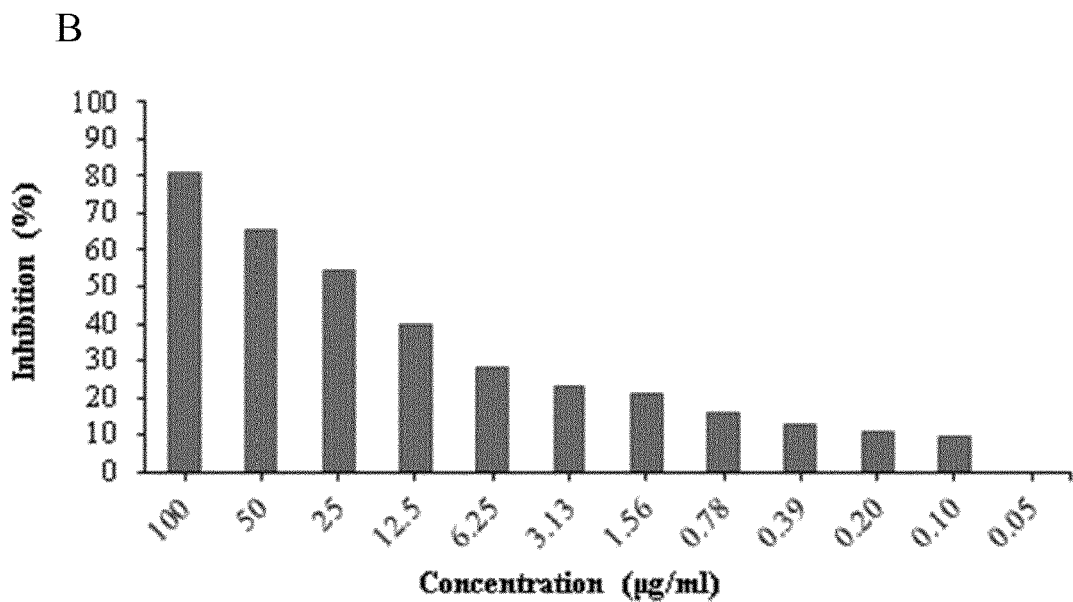
Fig. 6

NOROVIRUS ANTIBODIES

SEQUENCE LISTING

The present application contains a Sequence Listing which has been submitted electronically in ASCII format and is hereby incorporated by reference in its entirety. The ASCII copy, created on Sep. 14, 2018, is named 097147-0145_SL.txt and is 6,264 bytes in size.

FIELD OF THE INVENTION

The present invention relates to a binding polypeptide specifically binding to the amino acid sequence W-V-N-$X^1$-F-Y-$X^2$ (SEQ ID NO:1), wherein $X^1$ represents any amino acid, preferably Q or P, and wherein $X^2$ represents any amino acid, preferably, T or S in a norovirus polypeptide. The present invention further relates to polynucleotide encoding a binding polypeptide of the present invention, to a host cell comprising the same or the polynucleotide of the invention. The present invention further relates to a method of detecting the presence of a norovirus capsid polypeptide in a sample and to kits, devices, and uses making use of the binding peptide of the invention.

RELATED ART

Human noroviruses are single-stranded RNA, non-enveloped viruses in the Caliciviridae family and are the most important cause of outbreaks of gastroenteritis. These viruses cannot grow in cell culture, which has hampered vaccine and antiviral development. The genome has three open reading frames (ORF1-3), where ORF1 encodes the non-structural proteins (NS1 to NS7), ORF2 encodes the capsid protein (VP1), and ORF3 encodes a small structural protein. Expression of the capsid protein in insect cells leads to the self-assembly of empty virus-like particles (VLPs) that are morphologically and antigenically similar to native virions (Hansman, G. S., K. Natori, H. Shirato-Horikoshi, S. Ogawa, T. Oka, K. Katayama, T. Tanaka, T. Miyoshi, K. Sakae, S. Kobayashi, M. Shinohara, K. Uchida, N. Sakurai, K. Shinozaki, M. Okada, Y. Seto, K. Kamata, N. Nagata, K. Tanaka, T. Miyamura, and N. Takeda. 2006. Genetic and antigenic diversity among noroviruses. J Gen Virol 87:909-91). Based on the capsid gene sequences, at least five genogroups (GI-GV) have been assigned (Kroneman, A., E. Vega, H. Vennema, J. Vinje, P. A. White, G. Hansman, K. Green, V. Martella, K. Katayama, and M. Koopmans. 2013. Proposal for a unified norovirus nomenclature and genotyping. Arch Virol 158:2059-2068). The genogroups are further subdivided into genotypes and an association between genetic clusters and antigenicity is evident (Hansman et al., loc. cit.).

The X-ray crystal structure of the norovirus GI genotype 1 (GI.1) VLPs showed that VP1 is divided into two domains, shell (S) and protruding (P) (Prasad, B. V., M. E. Hardy, T. Dokland, J. Bella, M. G. Rossmann, and M. K. Estes. 1999. X-ray crystallographic structure of the Norwalk virus capsid. Science 286:287-290). The S domain forms a scaffold surrounding the RNA, whereas the P domain likely contains the determinants for strain diversity. One major structural distinction among these particles is the position of the P domain on the S domain. In the case of GI.1, the P domain is resting on the S domain, whereas in GV.1 and GII.10, the P domains are raised off the S domain by ~15 Å. In most noroviruses, the S and P domains are connected by a flexible hinge region, ~10 amino acids long, which allows for the raised P domains, but likely also permits a certain amount of P domain flexibility on the particles (Smith, T. J. 2011. Structural studies on antibody recognition and neutralization of viruses. Curr Opin Virol 1:150-156).

Little is known about antibody binding epitopes at the structural level. Recently, the first X-ray crystal structure of a norovirus P domain Fab complex was solved (Hansman, G. S., D. W. Taylor, J. S. McLellan, T. J. Smith, I. Georgiev, J. R. Tame, S. Y. Park, M. Yamazaki, F. Gondaira, M. Miki, K. Katayama, K. Murata, and P. D. Kwong. 2012. Structural basis for broad detection of genogroup II noroviruses by a monoclonal antibody that binds to a site occluded in the viral particle. Journal of virology 86:3635-3646; EP2757111A1). Superposition of the P domain Fab complex on the cryo-EM particle indicated the Fab bound to an occluded site on the particle, i.e., hindered by neighboring P domains. However, this broadly reactive monoclonal antibody recognizes a conserved region on the P domain and is used in a commercial diagnostic ELISA detection kit. Moreover, other monoclonal antibodies are thought to bind this occluded region on particles (Parker, T. D., N. Kitamoto, T. Tanaka, A. M. Hutson, and M. K. Estes. 2005. Identification of Genogroup I and Genogroup II broadly reactive epitopes on the norovirus capsid. Journal of virology 79:7402-7409; Prasad, B. V., R. Rothnagel, X. Jiang, and M. K. Estes. 1994. Three-dimensional structure of baculovirus-expressed Norwalk virus capsids. Journal of virology 68:5117-5125; Shiota, T., M. Okame, S. Takanashi, P. Khamrin, M. Takagi, K. Satou, Y. Masuoka, F. Yagyu, Y. Shimizu, H. Kohno, M. Mizuguchi, S. Okitsu, and H. Ushijima. 2007. Characterization of a broadly reactive monoclonal antibody against norovirus genogroups I and II: recognition of a novel conformational epitope. Journal of virology 81:12298-12306). This suggested the occluded region was not only immunoreactive, but also immunodominant.

Despite the described progress toward broadly-reactive antibodies, antibodies suitable in preventing norovirus infection and antibodies permitting broad detection of norovirus strains are still needed. There is, thus, a need in the art for improved antibodies solving the problems as described above.

Problem to be Solved

It is therefore an objective of the present invention to provide improved antibodies avoiding the problems as described above.

SUMMARY OF THE INVENTION

These problems are solved by the binding polypeptides, polynucleotides, methods, kits, devices, and compositions with the features of the independent claims. Typical embodiments, which might be realized in an isolated fashion or in any arbitrary combination are listed in the dependent claims.

Accordingly, the present invention relates to a binding polypeptide specifically binding to the amino acid sequence W-V-N-$X^1$-F-Y-$X^2$ (SEQ ID NO:1), wherein $X^1$ represents any amino acid, preferably Q or P, and wherein $X^2$ represents any amino acid, preferably, T or S in a norovirus polypeptide.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention. The term "about" in the context of specific values or ratios of the present invention refers to said value or ratio +/−30%, +/−20%, +/−10%, or, in an embodiment +/−5% of a given value or ratio.

The term "polypeptide" is known to the skilled person and relates to a chemical compound comprising, preferably consisting of, amino acids chemically bonded by peptide bonds. Preferably, said amino acids are L-amino acids; more preferably L-amino acids cotranslationally inserted in a polypeptide. The polypeptide may be synthesized chemically, in vitro, or in a biological expression system.

The term, "binding polypeptide", as used herein, relates to a polypeptide specifically binding to the amino acid sequence W-V-N-$X^1$-F-Y-$X^2$ (SEQ ID NO:1), wherein $X^1$ represents any amino acid, preferably Q or P, and wherein $X^2$ represents any amino acid, preferably, T or S in a norovirus polypeptide. More preferably, the binding polypeptide binds to the amino acid sequence (i) F-$X^6$-$X^5$-$X^4$-$X^3$-W-V-N-$X^1$-F-Y-$X^2$ (SEQ ID NO:2), (ii) $X^{53}X^{52}$ . . . $X^3$-W-V-N-$X^1$-F-Y-$X^2$ (SEQ ID NO:3); and/or (iii) $X^{53}$ $X^{52}$ . . . $X^8$-F-$X^6$-$X^5$-$X^4$-$X^3$-W-V-N-$X^1$-F-Y-$X^2$ (SEQ ID NO:4), wherein $X^3$ to $X^{52}$ represent any amino acid and wherein $X^{53}$ represents a non-charged amino acid, preferably, L, P, M, Q, or N. It is understood by the skilled person that the notation $X^n$ . . . $X^m$ relates to $X^n$, $X^{n+1}$, $X^{n+2}$, $X^{n+3}$, . . . $X^{m-1}$, $X^m$. Preferably, the binding polypeptide binds to the norovirus polypeptide of the present invention with sufficient affinity to allow detection of a binding polypeptide/norovirus polypeptide complex. Preferably, the dissociation constant ($K_d$) of the binding polypeptide/norovirus polypeptide complex is at most $10^{-7}$ mol/L, more preferably, at most $10^{-8}$ mol/l, most preferably, at most $10^{-9}$ mol/L.

The term "specifically binding" is understood by the skilled person. Preferably, specific binding relates to a binding in which the affinity of the binding polypeptide to a norovirus capsid polypeptide, preferably a norovirus polypeptide as specified elsewhere herein, is at least tenfold, preferably at least 100 fold, most preferably at least 1000 fold higher than for any non-target polypeptide or non-norovirus polypeptide present in a sample. Accordingly, the dissociation constant ($K_d$) of any binding polypeptide/non-target polypeptide complex is at least $10^{-4}$ mol/L, more preferably, at least $10^{-5}$ mol/l, most preferably, at least $10^{-6}$ mol/L.

Preferably, the binding polypeptide of the present invention is an antibody. The term "antibody" is used herein in the broadest sense and specifically covers monoclonal antibodies, polyclonal antibodies, multispecific antibodies (e.g. bispecific antibodies) formed from at least two intact antibodies, single-domain-antibodies (VHH), also known as Nanobodies, and antibody fragments so long as they exhibit the desired binding activity as specified elsewhere herein. Preferably, an antibody is not an antibody comprised in an antiserum, typically not a polyclonal antibody or a polyclonal serum. Preferably, the antibody is a full-length antibody or an antibody fragment. More preferably, the antibody is a monoclonal antibody. Most preferably, the antibody is a VHH (Nanobody).

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

"Antibody fragments" comprise a portion of an intact antibody, in an embodiment, comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. Preferably, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs, also referred to as complementarity determining regions (CDRs)) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Preferably, such a monoclonal antibody includes an antibody comprising a polypeptide sequence that binds a norovirus polypeptide, wherein the target-binding polypeptide sequence was obtained by a process that includes the selection of a single binding polypeptide sequence from a plurality of polypeptide sequences. For example, the selection process can be the selection of a unique clone from a plurality of clones, such as a pool of hybridoma clones, phage clones, or recombinant DNA clones.

The term "single-domain antibody" (VHH) or "Nanobody", relates to an antibody fragment comprising one variable antibody domain and is, in principle, known to the skilled person. A review is provided, e.g. in Muyldermanns et al. (2009), Vet Immunol Immunopathol. 128(1-3):178. Preferably, the VHH comprises the CDRs of a heavy-chain antibody, preferably obtained from a dromedar, camel, llama, or shark immunized with a target polypeptide. More preferably, the VHH has the binding properties as specified above. Still more preferably, the VHH comprises the CDRs: CDR1: GSIFSIYA (SEQ ID NO:6), CDR2: ISSGGGTN (SEQ ID NO:7), and CDR3: KREDYSAYAPPSGS (SEQ ID NO:8). Most preferably, the VHH is a polypeptide comprising the amino acid sequence of SEQ ID NO:9.

It is understood by the skilled person that the binding properties of an antibody, in particular of a VHH, usually are conserved if amino acids, in particular those not comprised in a CDR, are exchanged. Accordingly, the term binding polypeptide also relates to polypeptides comprising an amino acid sequence having at least 70%, more preferably at least 80%, still more preferably at least 90%, even more preferably at least 95%, most preferably at least 99%, sequence identity to SEQ ID NO:9 and having the property of specifically binding the norovirus polypeptide according to the present invention. More preferably, term binding polypeptide also relates to polypeptides comprising an amino acid sequence having at least 70% sequence identity to SEQ ID NO:9 and comprising CDR1, CDR2, and/or CDR3 as specified above, preferably located within the sequence at about the same position(s) as in SEQ ID NO:9. Such exchanges of amino acids and variants can e.g. be used for providing a humanized binding polypeptide or a binding polypeptide resistant to acid or enzymatic cleavage.

Also, preferably, the binding polypeptide may be, preferably covalently, linked to a chemical molecule. Methods how to covalently link a polypeptide with a chemical molecule are known in the art. Preferred chemical molecules for covalently linking with the binding polypeptide of the present invention are polymers like, e.g. polyethylene glycol, polysaccharides such as starch or one of its derivatives, targeting molecules, and the like.

Moreover, the binding polypeptide may be a fusion polypeptide comprising a further polypeptide portion with a further functionality. E.g. said fusion polypeptide may comprise a linker and/or a tag. As used herein, the term "tag" relates to a detectable chemical or physical moiety covalently connected with the binding polypeptide of the present invention. In an aspect, the tag is an affinity tag or, preferably, a hapten, i.e. a tag having affinity to an affinity compound. In yet a further aspect, the binding of the affinity tag to the affinity compound has a dissociation constant so low that the affinity tag will only dissociate to a negligible extent from the affinity compound. In a yet further aspect, the dissociation constant of the affinity tag:affinity compound pair is less than 10-5 mol/l (as it is the case with the Strep-Tag:Strep-Tactin binding), less than $10^{-6}$ mol/l (as it is the case in the Strep-TagII:Strep-Tactin binding), less than $10^{-7}$ mol/l (as it is typically the case in antibody:antigen binding), less than $10^{-8}$ mol/l, less than $10^{-10}$ mol/l, or less than $10^{-12}$ mol/l (as it is the case for the Streptavidin:Biotin binding). E.g., preferably, hapten-conjugated nanobodies may be used for the detection of bound norovirus polypeptide or nanovirus particles, preferably in combination with specific conjugates like peroxidase labeled streptavidin. Methods of determining dissociation constants are well known to the skilled artisan and include, e.g., spectroscopic titration methods, surface plasmon resonance measurements, equilibrium dialysis and the like. Preferably, the affinity tag is a His-tag, Strep-tag, V5-tag, Myc-tag, HA-tag, FLAG-tag, or GST. More preferably, the tag is an enzymatic marker tag, i.e. a tag having an enzymatic activity determinable under appropriate conditions. Suitable enzymatic marker tags are well known in the art and include, e.g. horseradish peroxidase, alkaline phosphatase, luciferase, or beta-galactosidase, and the like. In another aspect, the term tag relates to a fluorescent protein tag. Fluorescent protein tags are well known in the art and include the fluorescent proteins from various organisms, e.g. *Aequorea victoria, Verrillofungia concinna, Lobophyllia hemprichii, Goniastrea australensis, Favia favus*, and the like, as well as derivatives having a wildtype or a modified excitation- and/or emission-spectrum, like GFP, eGFP, YFP, CFP, or RFP. It is understood by the skilled person that a tag of the present invention is not necessarily restricted to one of the categories as detailed above; e.g. an enzymatic marker tag or a fluorescent protein tag may also be used as an affinity tag, e.g. by using an appropriate antibody recognizing said enzymatic marker tag or fluorescent protein tag. Preferably, the tag is genetically encoded, i.e. the tag is provided as the encoding polynucleotide.

Methods for determining the amount of a fusion polypeptide comprising a tag as described herein are well known in the art and depend on the kind of tag used. In a preferred embodiment, a hapten may be used to either coat a solid phase like magnetic particles or microtiter plates. Preferably, the amount of a tagged cleavage product comprising an enzymatic marker tag is determined by incubating a sample comprising said enzymatic marker tag with an appropriate substrate, the product of which produced by the enzymatic action of said enzymatic marker tag can be determined. Examples of substrate/enzymatic marker pairs include 3,3', 5,5'-Tetramethylbenzidine (TMB), 3,3'-Diaminobenzidine (DAB), or 2,2'-Azino-bis(3-ethylbenzothiazoline-6-sulphonic acid) (ABTS) conversion by horseradish peroxidase; 4-Methylumbelliferyl phosphate (4-MUP) or p-Nitrophenyl phosphate conversion by alkaline phosphatase; luciferin conversion by luciferase; or 5-Bromo-4-chloro-indolyl-β-D-galactopyranoside conversion by beta-galactosidase. Also preferably, the amount of a tag comprising a fluorescent protein tag is determined by illuminating said fluorescent protein tag at an appropriate wavelength and determining absorbance or fluorescence of the tag. It is understood by the skilled person that practically any tag can be determined by immunological methods, provided that a specific antibody for said tag is available or can be generated.

The term "norovirus polypeptide", as used herein, relates to a norovirus polypeptide comprising the target amino acid sequence W-V-N-$X^1$-F-Y-$X^2$ (SEQ ID NO:1), wherein $X^1$ represents any amino acid, preferably Q or P, and wherein $X^2$ represents any amino acid, preferably, T or S. More preferably, the norovirus polypeptide comprises the target amino acid sequence (i) F-$X^6$-$X^5$-$X^4$-$X^3$-W-V-N-$X^1$-F-Y-$X^2$ (SEQ ID NO:2), (ii) $X^{53}X^{52}$ . . . $X^3$-W-V-N-$X^1$-F-Y-$X^2$ (SEQ ID NO:3); and/or (iii) $X^{53}X^{52}$ . . . $X^8$-F-$X^6$-$X^5$-$X^4$-$X^3$-W-V-N-$X^1$-F-Y-$X^2$ (SEQ ID NO:4), wherein $X^3$ to $X^{52}$ represent any amino acid and wherein $X^{53}$ represents a non-charged amino acid, preferably, L, P, M, Q, or N.

Preferably, the norovirus polypeptide is a polypeptide comprising at least one of said target amino acid sequences. Preferably, the norovirus polypeptide is a structural component of a virus, preferably a capsid polypeptide. Accordingly, most preferably, the norovirus polypeptide is a norovirus capsid polypeptide.

The term "norovirus" is, in principle, known to the skilled person, and relates to a member of the genetically diverse group of non-enveloped, single-stranded RNA viruses of the Caliciviridae family. Preferably, the norovirus is a genogroup GII or GI norovirus. More preferably, the norovirus is a genogroup GII norovirus. Preferably, the norovirus is a GU, GII.2, GII.3, GII.5, GII.6, GII.7, or GII.8. More preferably, the norovirus is norovirus GII.1, GII.4, GII.12, or GII.10.

Advantageously, it was found in the work underlying the present invention that the binding polypeptide of the present invention has the capacity of broadly recognizing at least all genogroup II members of the genus norovirus, as well as several members of the genogroup I. Accordingly, such an antibody can be used in diagnostic tests screening broadly for norovirus infection. Moreover, said antibody has the potential to be used for inhibiting norovirus infection without the need to know which genotype. Moreover, it was found that the antibody if the present invention can inactivate norovirus particles by binding to the specific site indicated, and thereby prevent further spread of an infection. Advantageously, it is also envisaged to use the binding polypeptide of the present invention for sanitization and disinfection purposes. In particular, the nanobody of the present invention was found to also recognize members of genogroup I. Since nanobodies are easy and cost-effective to produce, this offers the possibility to provide norovirus detection kits at low cost. Moreover, since nanobodies are small and can be applied at high densities onto solid surfaces, the sensitivity of norovirus-assays can be improved. The small size of nanobodies is, preferably, particularly advantageous e.g. in immunochromatography, since it allows for applying a high molar concentration of antibody onto a limited space; therefore, preferably, a combination of several nanobodies may be used to increase the range of detectable genotypes while not compromising sensitivity.

The definitions made above apply mutatis mutandis to the following. Additional definitions and explanations made further below also apply for all embodiments described in this specification mutatis mutandis.

The present invention also relates to a polynucleotide encoding a binding polypeptide according to the present invention
(i) encoding a binding polypeptide comprising an amino acid sequence of SEQ ID NO: 9,
(ii) comprising a nucleotide sequence as shown in SEQ ID NO: 5,
(iii) encoding a binding polypeptide comprising an amino acid sequence having at least 70% sequence identity to SEQ ID NO:9, or/and
(iv) comprising a nucleotide sequence having at least 70% sequence identity to a nucleotide sequence as shown in SEQ ID NO:5.

The term "polynucleotide", as used in accordance with the present invention, relates to a polynucleotide comprising a nucleic acid sequence which encodes a polypeptide having the biological property of specifically binding to a norovirus polypeptide as specified herein above. Suitable assays for measuring the activities mentioned before are described in the accompanying Examples or in standard literature. A polynucleotide encoding a polypeptide having the aforementioned biological activity has been obtained in accordance with the present invention from an alpaca. The polynucleotide, preferably, comprises the nucleic acid sequence shown in SEQ ID NO:5 encoding the polypeptide having an amino acid sequence as shown in SEQ ID NO:9. It is to be understood that a polypeptide having an amino acid sequence as shown in SEQ ID NO:9 may be also encoded, due to the degenerated genetic code, by other polynucleotides as well. It is also understood that, depending on the specific expression system selected, adaptation of codon usage may improve yields.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences shown in SEQ ID NO:5 by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6' sodium chloride/sodium citrate (=SSC) at approximately 45° C., followed by one or more wash steps in 0.2' SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5' SSC (pH 7.2). If organic solvent is present in the abovementioned buffer, for example 50% formamide, the temperature under standard conditions is approximately 42° C. The hybridization conditions for DNA:DNA hybrids are preferably for example 0.1' SSC and 20° C. to 45° C., preferably between 30° C. and 45° C. The hybridization conditions for DNA:RNA hybrids are preferably, for example, 0.1' SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Further, variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO:5. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO:9. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has the activity as specified above. Accordingly, the polypeptide encoded may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags (SEQ ID NO: 15), MYC-tags and the like.

The polynucleotide of the present invention shall be provided, preferably, either as an isolated polynucleotide (i.e. isolated from its natural context) or in genetically modified form. The polynucleotide, preferably, is DNA, including cDNA, or RNA. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides.

The present invention further relates to a host cell comprising the binding polypeptide or the polynucleotide of the present invention.

The term "host cell", as used herein, relates to a an eukaryotic or, preferably, prokaryotic cell. Preferably, the cell is a cultured cell of a mammal, more preferably a human cell. More preferably, the cell is a bacterial or fungal cell, still more preferably an *Escherichia coli* cell.

The present invention also relates to a binding polypeptide according to the present invention for use in diagnosing a norovirus-infection in a sample of a subject.

The term "diagnosing", as used herein, refers to assessing the probability according to which a subject is suffering or will suffer from a disease or condition referred to in this specification, in particular norovirus infection. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population.

The term "subject" as referred to herein encompasses animals which can be infected by a norovirus, preferably mammals, and, more preferably, humans. More preferably, said subject suffers from, is suspected to suffer from, or is at risk to suffer from a norovirus infection. It will be understood that said term, preferably, includes subjects suspected to be asymptomatic norovirus carriers. Subjects which suffer from the said infection can be identified by the accompanying symptoms known for the disease. These symptoms are known in the art and described, e.g., in standard text books. A subject suspect to suffer from the aforementioned disease may be any apparently healthy subject, e.g., investigated by routine clinical screening, or may be a subject being at risk for developing the aforementioned disease.

The present invention also relates to a binding polypeptide according to the present invention for use in treating and/or preventing a norovirus infection in a subject.

The term "treating" refers to ameliorating the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools as described herein above.

The term "preventing" refers to retaining health with respect to the diseases or disorders referred to herein for a certain period of time in a subject. It will be understood that the said period of time is dependent on the amount of the binding polypeptide which has been administered and individual factors of the subject discussed elsewhere in this specification. It is to be understood that prevention may not be effective in all subjects treated with the compound according to the present invention. However, the term requires that a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed elsewhere in this specification.

The present invention further relates to the use of the binding polypeptide according to the present invention for diagnosing, treating and/or preventing a norovirus-infection. Moreover, the present invention relates to use of the binding polypeptide according to the present invention for inactivating a norovirus particle.

As used herein, the term "inactivating a norovirus particle" relates to inducing a, preferably irreversible, change in the structure and/or composition of the norovirus particle causing the norovirus particle to become non-infectious and/or replication incompetent. Preferably, inactivating is preventing the norovirus particle from binding to its cognate receptor, preventing the norovirus particle from unpacking its genome, or destroying the structure of the norovirus particle.

Furthermore, the present invention relates to a method of detecting the presence of a norovirus capsid polypeptide in a sample, comprising
(a) contacting said sample to a binding polypeptide of the present invention,
(b) detecting the amount of binding polypeptide/norovirus capsid polypeptide complexes in said sample, thereby
(c) detecting the presence of norovirus capsid polypeptides in said sample.

The method of detecting the presence of a norovirus capsid polypeptide of the present invention, preferably, is an in vitro method. Moreover, it may comprise steps in addition to those explicitly mentioned above. For example, further steps may relate, e.g., to taking or providing a sample for step a), or contacting the binding polypeptide/norovirus capsid polypeptide complexes from step b) to a detection agent. Moreover, one or more of said steps may be performed by automated equipment. Also, preferably, detecting the presence of a norovirus capsid polypeptide is detecting the presence of norovirus particles. Accordingly, detecting the presence of a norovirus capsid polypeptide in a sample from a subject, preferably, is indicative of a norovirus infection prevalent in said subject. Thus, the method of detecting the presence of a norovirus capsid polypeptide, preferably, is a method of diagnosing a norovirus infection.

The term "sample", as used herein, refers to any sample suspected or known to comprise a norovirus capsid polypeptide. It envisaged according to the present invention that the sample may be, e.g. a food sample, a swab from a surface in a kitchen, or a sample of cell culture supernatant. Preferably, however, the sample is a sample of a body fluid, a sample of separated cells, a sample from a tissue or an organ, or a sample of wash/rinse fluid obtained from an outer or inner body surface of a subject. More preferably, the sample is body fluids like blood, plasma, serum, urine, saliva, or lacrimal fluid. Most preferably, the sample is a stool sample. Samples can be obtained by well known techniques and include, preferably, scrapes, swabs or biopsies. Such samples can be obtained by use of brushes, (cotton) swabs, spatula, rinse/wash fluids, punch biopsy devices, puncture of cavities with needles or surgical instrumentation. Preferably, the sample originates from blood or liver. More preferably, the sample originates from the urogenital tract, the oral cavity, the upper aerodigestive tract and the epidermis. Most preferably, the sample originates from the anal canal. Separated cells and/or cell-free liquids may be obtained from cell culture supernatants, body fluids, or the tissues or organs by separating techniques such as filtration, centrifugation, or cell sorting. Separated cells, preferably, are lysed before being used as samples in the present invention by one of the methods well known to the skilled artisan. It is to be understood that the sample may be further processed in order to carry out the method of the present invention.

The term "contacting" as used in the context of the methods of the present invention is understood by the skilled person. Preferably, the term relates to bringing a binding polypeptide of the present invention in physical contact with a sample and thereby, e.g. allowing the sample and the binding polypeptide to interact. Preferably, contacting is performed under conditions allowing stable interaction between a binding polypeptide and a norovirus polypeptide.

The amount of binding polypeptide/norovirus capsid polypeptide can be determined in a sample of a subject by techniques well known in the art, including those described herein above. Depending on the nature of the sample, the amount may be determined by ELISA based techniques or by an immunochromatography method. To this end, antibodies or aptamers may be used as detection agents which specifically bind to at least one component of the binding polypeptide/norovirus capsid polypeptide and which, upon binding, can be detected by a detectable label. How such antibodies or aptamers can be generated is known to the skilled person. A detectable label may be covalently or reversibly linked to the antibody or aptamer. A covalently linked label may be a radioactive, fluorophore or chemiluminescent moiety while a reversible label may be a secondary antibody or an aptamer which specifically binds to the detection agent and which upon binding can be used to detect the bound detection agent.

The present invention also relates to a method of treating a norovirus infection in a subject, comprising
(a) contacting said subject to a binding polypeptide according to the present invention, thereby
(b) treating said norovirus infection in said subject.

The method of treating a norovirus infection of the present invention, preferably, is an in vivo method. Moreover, it may comprise steps in addition to those explicitly mentioned above. For example, further steps may relate, e.g., to diagnosing a norovirus infection, preferably according to the method of detecting the presence of a norovirus capsid polypeptide of the present invention before step a), or administering a further pharmaceutically active compound to said subject. Moreover, one or more of said steps may be performed by automated equipment.

Contacting a subject with the binding polypeptide of the present invention, preferably, is administering said binding polypeptide comprised in a pharmaceutical composition. The term "pharmaceutical composition", as used herein, relates to a mixture of pharmaceutically acceptable compounds comprising at least the binding polypeptide of the present invention and optionally one or more pharmaceutically acceptable carrier. The binding polypeptide of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. Preferably, administration is peroral. However, depending on the nature and mode of action of a compound, the pharmaceutical compositions may be administered by other routes as well. Moreover, the binding polypeptide can be administered in combination with other drugs either in a common pharmaceutical composition or as separated pharmaceutical compositions wherein said separated pharmaceutical compositions may be provided in form of a kit of parts.

The binding polypeptide is, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. Preferably, in case of peroral administration, a preparation comprising an acid-resistant coating is used.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

A therapeutically effective dose refers to an amount of the binding polypeptide to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 1 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

Moreover, the present invention relates to a method of preventing a norovirus infection, comprising
(a) contacting an object suspected to comprise a norovirus particle or a subject at risk of becoming infected with a norovirus with a binding polypeptide according to the present invention, thereby
(b) preventing a norovirus infection.

The method of preventing a norovirus infection of the present invention, preferably, is an in vitro method; It may, however, also be performed in vivo, e.g. by prophylactically administering the binding polypeptide of the present invention to a subject. Moreover, it may comprise steps in addition to those explicitly mentioned above. For example, further steps may relate, e.g., to estimating the risk of a subject of becoming infected by a norovirus before step a), or applying further chemical compounds, e.g. disinfectants, to an object. Moreover, one or more of said steps may be performed by automated equipment.

For the method of preventing a norovirus infection by contacting a subject at risk of becoming infected, the definitions provided for the method of treating a norovirus infection in a subject provided herein above apply mutatis mutandis. As will be understood by the skilled person, preventing in such case may also include treating the skin of the hands with the binding polypeptide of the present invention.

For the method of preventing a norovirus infection by contacting object suspected to comprise a norovirus particle, it is envisaged that the binding polypeptide of the present invention is applied to said object in order to inactivate viral particles potentially comprised on its surface or therein. Accordingly, the term "object", as used herein, relates to any physical object suspected to comprise norovirus particles. Preferably, said object is a part of the equipment of a lavatory, e.g. a toilet seat, a toilet bowl, a basin, or a faucet. It is, however, also envisaged that the object is an object in another area at high risk of norovirus spread, e.g. equipment and surfaces in a canteen kitchen.

Moreover, the present invention relates to a use of a binding polypeptide according to the present invention for the manufacture of a diagnostic compound, kit, or device for diagnosing a norovirus infection; and to a use of a binding polypeptide according to the present invention for the manufacture of a therapeutic composition kit, or device for the treatment of a norovirus infection.

The present invention also relates to a kit for diagnosing, preventing or/and treating a norovirus infection, comprising the binding polypeptide of the present invention in a housing.

The term "kit" as used herein refers to a collection of the aforementioned means, e.g., a composition comprising the binding polypeptide of the current invention and/or means for contacting a sample under conditions which allow for forming complexes between said binding polypeptide and a norovirus polypeptide, preferably, provided separately or within a single container. The container, also preferably, comprises instructions for carrying out the method of the present invention. The components of the kit are provided, preferably, in a "ready-to-use" manner, e.g., concentrations are adjusted accordingly, etc.

The present invention also relates to a device for diagnosing a norovirus infection, comprising the binding polypeptide of the present invention and means for determining the amount of binding polypeptide/norovirus polypeptide complex formed in the presence of a sample.

The term "device" as used herein in the context of a device for diagnosing a norovirus infection relates to a system of means comprising at least the means operatively linked to each other as to allow the diagnosis. Preferred means for determining the amount of binding polypeptide/norovirus polypeptide formed in the presence of a sample are well known in the art. How to link the means in an operating manner will depend on the type of means included into the device. Preferably, the means are comprised by a single device in such a case. Said device may accordingly include a detection unit and a computer unit for processing data obtained from the detection unit for determining the amount of binding polypeptide/norovirus polypeptide complex. However, it is also contemplated that the means of the current invention may appear as separate devices in such an embodiment and are, preferably, packaged together as a kit. The person skilled in the art will realize how to link the means without further ado. Preferred devices are those which can be applied without the particular knowledge of a specialized technician.

Moreover, the present invention relates to a device for preventing or/and treating a norovirus infection, comprising the binding polypeptide of any one the present invention and means for administering the same.

The term "device", as used herein in the context of a device for preventing or/and treating a norovirus infection, relates to a system of means comprising at least the means operatively linked to each other as to allow administration of the compound or of the medicament of the present invention. Preferred means for administering medicaments are well known in the art. How to link the means in an operating manner will depend on the type of means included into the device and on the kind of administration envisaged. Preferably, the means are comprised by a single device in such a case. Said device may accordingly include a delivery unit for the administration of the compound or medicament and a storage unit for storing said compound or medicament until administration. However, it is also contemplated that the means of the current invention may appear as separate devices in such an embodiment and are, preferably, packaged together as a kit. The person skilled in the art will realize how to link the means without further ado. Preferred devices are those which can be applied without the particular knowledge of a specialized technician. In a preferred embodiment, the device is a syringe, more preferably with a needle, comprising the compound or medicament of the invention. In another preferred embodiment, the device is an intravenous infusion (IV) equipment comprising the compound or medicament. In another preferred embodiment, the device is an endoscopic device comprising the compound or medicament for flushing a site of norovirus infection. In still another preferred embodiment the device is an inhaler comprising the compound of the present invention, wherein, more preferably, said compound is formulated for administration as an aerosol.

All references cited in this specification are herewith incorporated by reference with respect to their entire disclosure content and the disclosure content specifically mentioned in this specification.

In view of the above, the following embodiments are preferred:

Embodiment 1

A binding polypeptide specifically binding to the amino acid sequence W-V-N-$X^1$-F-Y-$X^2$ (SEQ ID NO:1), wherein $X^1$ represents any amino acid, preferably Q or P, and wherein $X^2$ represents any amino acid, preferably, T or S in a norovirus polypeptide.

Embodiment 2

The binding polypeptide of embodiment 1, wherein said binding polypeptide is an antibody.

Embodiment 3

The binding polypeptide of embodiment 1 or 2, wherein said binding polypeptide is a single-domain antibody (VHH).

Embodiment 4

The binding polypeptide of any one of embodiments 1 to 3, wherein said binding polypeptide specifically binds to the sequence (i)

$$\text{F-}X^6\text{-}X^5\text{-}X^4\text{-}X^3\text{-W-V-N-}X^1\text{-F-Y-}X^2, \quad \text{(SEQ ID NO: 2)}$$

(ii)

$$X^{53}X^{52}\ldots X^3\text{-W-V-N-}X^1\text{-F-Y-}X^2; \quad \text{(SEQ ID NO: 3)}$$

and/or (iii)

$$X^{53}X^{52}\ldots X^8\text{-F-}X^6\text{-}X^5\text{-}X^4\text{-}X^3\text{-W-V-N-}X^1\text{-F-Y-}X^2, \quad \text{(SEQ ID NO: 4)}$$

wherein $X^3$ to $X^{52}$ represent any amino acid and wherein $X^{53}$ represents a non-charged amino acid, preferably, L, P, M, Q, or N.

Embodiment 5

The binding polypeptide of any one of embodiments 1 to 4, wherein said binding polypeptide competes in binding to a capsid polypeptide of a norovirus genogroup II (GII) with a VHH encoded by SEQ ID NO:5.

Embodiment 6

The binding polypeptide of any one of embodiments 1 to 5, wherein said norovirus polypeptide is a norovirus capsid polypeptide.

Embodiment 7

The binding polypeptide of any one of embodiments 1 to 6, wherein said binding polypeptide comprises the complementarity determining regions (CDRs) GSIFSIYA (SEQ ID NO:6), ISSGGGTN (SEQ ID NO:7), and KREDYSAY-APPSGS (SEQ ID NO:8).

Embodiment 8

The binding polypeptide of any one of embodiments 1 to 7, wherein said binding polypeptide comprises an amino acid sequence essentially having the amino acid sequence of SEQ ID NO:9; preferably wherein said binding polypeptide comprises an amino acid sequence having the amino acid sequence of SEQ ID NO:9 or comprises an amino acid sequence having at least 70% sequence identity to SEQ ID NO:9.

Embodiment 9

A polynucleotide encoding a binding polypeptide according to any one of embodiments 1 to 8
(i) encoding a binding polypeptide comprising an amino acid sequence of SEQ ID NO: 9,
(ii) comprising a nucleotide sequence as shown in SEQ ID NO: 5,
(iii) encoding a binding polypeptide comprising an amino acid sequence having at least 70% sequence identity to SEQ ID NO:9, or/and
(iv) comprising a nucleotide sequence having at least 70% sequence identity to a nucleotide sequence as shown in SEQ ID NO:5.

Embodiment 10

A host cell comprising the binding polypeptide according to any one of embodiments 1 to 8 or the polynucleotide according to embodiment 9.

Embodiment 11

A binding polypeptide according to any one of embodiments 1 to 8, for use in diagnosing a norovirus-infection in a sample of a subject.

Embodiment 12

A binding polypeptide according to any one of embodiments 1 to 8, for use in treating and/or preventing a norovirus-infection in a subject.

Embodiment 13

Use of the binding polypeptide according to any one of embodiments 1 to 8 for diagnosing, treating and/or preventing a norovirus-infection.

Embodiment 14

Use of the binding polypeptide according to any one of embodiments 1 to 8 for inactivating a norovirus particle.

Embodiment 15

A method of detecting the presence of a norovirus capsid polypeptide in a sample, comprising
(a) contacting said sample to a binding polypeptide according to any one of embodiments 1 to 8,
(b) detecting the amount of binding polypeptide/norovirus capsid polypeptide complexes in said sample, thereby
(c) detecting the presence of norovirus capsid polypeptides in said sample.

Embodiment 16

The method of embodiment 15, wherein said sample is a sample of a subject.

Embodiment 17

A method of treating a norovirus infection in a subject, comprising
(a) contacting said subject to a binding polypeptide according to any one of embodiments 1 to 8, thereby
(b) treating said norovirus infection in said subject.

Embodiment 18

A method of preventing a norovirus infection, comprising
(a) contacting an object suspected to comprise a norovirus particle with a binding polypeptide according to any one of embodiments 1 to 8, thereby
(b) preventing a norovirus infection.

Embodiment 19

Use of a binding polypeptide according to any one of embodiments 1 to 8 for the manufacture of a diagnostic compound, kit, or device for diagnosing a norovirus infection.

Embodiment 20

Use of a binding polypeptide according to any one of embodiments 1 to 8 for the manufacture of a therapeutic composition kit, or device for the treatment of a norovirus infection.

Embodiment 21

A kit for diagnosing, preventing or/and treating a norovirus infection, comprising the binding polypeptide of any one of embodiments 1 to 8 in a housing.

Embodiment 22

A device for diagnosing a norovirus infection, comprising the binding polypeptide of any one of embodiments 1 to 8 and means for determining the amount binding polypeptide/norovirus polypeptide complexes formed in the presence of a sample.

Embodiment 23

A device for preventing or/and treating a norovirus infection, comprising the binding polypeptide of any one of embodiments 1 to 8 and means for administering the same.

Embodiment 24

A vaccine comprising a peptide comprising the amino acid sequence W-V-N-$X^1$T-Y-$X^2$ (SEQ ID NO:1), wherein $X^1$ represents any amino acid, preferably Q or P, and wherein $X^2$ represents any amino acid, preferably, T or S.

Embodiment 25

The vaccine of embodiment 24, wherein said vaccine consists of at most 100, preferably at most 50, more preferably at most 25 amino acids.

Embodiment 26

The binding polypeptide of embodiment 1 to 6, wherein said binding polypeptide is an antibody fragment.

Embodiment 27

The binding polypeptide of embodiment 26, wherein said binding polypeptide is an Fab fragment, an Fab' fragment, an Fv fragment, a single-chain Fv antibody, or a single-domain antibody (VHH).

Embodiment 28

The binding polypeptide of embodiment 26 or 27, wherein said binding polypeptide is a single-domain antibody (VHH).

Embodiment 29

The binding polypeptide for use of embodiment 12, the use of embodiment 13, 14, 19, or 20, the method of any one of embodiments 15 to 18, the kit of embodiment 21, or the device of embodiment 22 or 23, wherein said binding polypeptide is a binding polypeptide according to embodiment 27 or 28.

FIGURE LEGENDS

FIG. 1: A) Direct ELISA. of norovirus virus like particles (VLPs) with nano-85. Nano-85 detected GII.10 VLPs at a dilution of 64,000, GII.4 and GII.12 VLPs at a dilution of 32,000 and GI.1 VLPs at a lower dilution of 4,000. X-axis: dilution, Y-axis: Absorption. B) As in A), but indirect ELISA.

Figure 2:
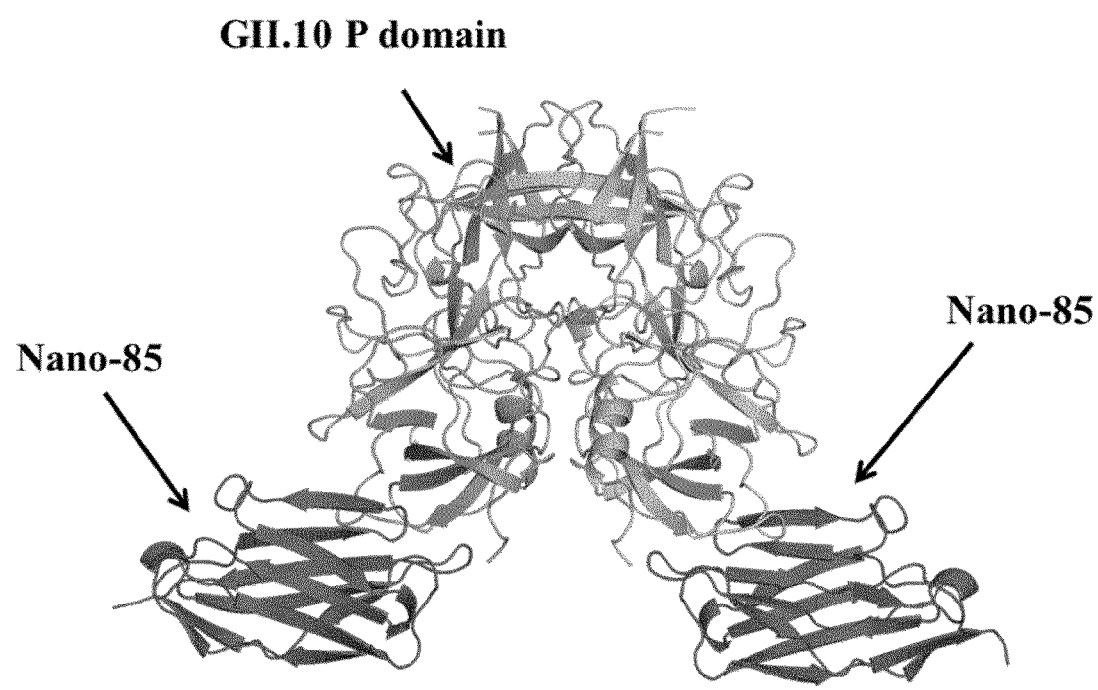
Figure 2B:
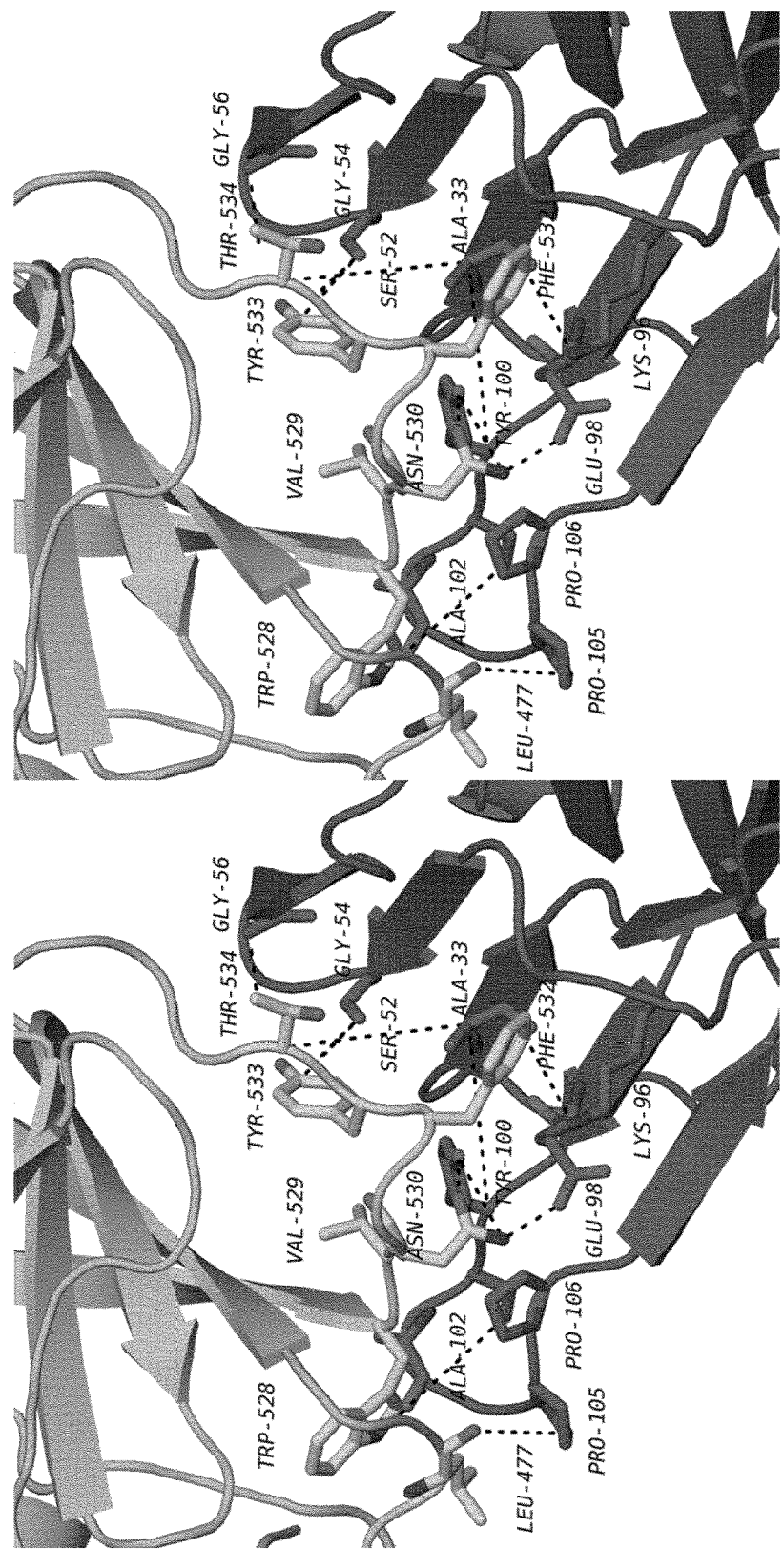

FIG. 2: A. Cartoon view of nano-85 bound to the lower region of the GII.10 P domain. B. Stereo view of A). A network of interactions is responsible for tight binding.

FIG. 3: A) amino acid sequence (SEQ ID NO: 9) of a single-domain antibody of the present invention; CDR sequences are underlined; B) exemplary nucleic acid sequence (SEQ ID NO: 5) encoding the single-domain antibody of A).

Figure 4:
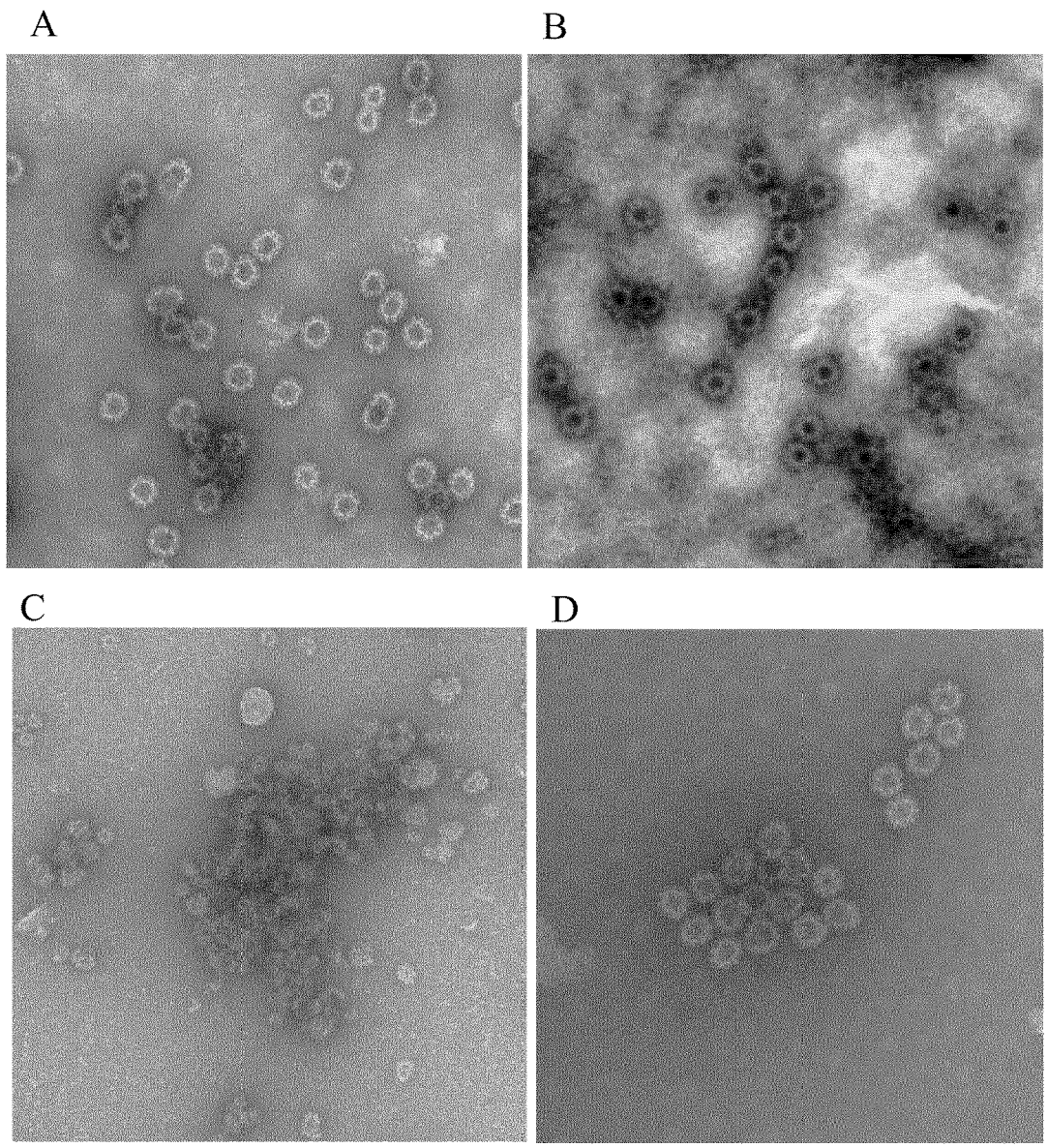

FIG. 4: Electron microscopy of GII.10 norovirus virus-like particles pretreated at an approx. 1:1 molar ratio with different antibodies; samples were applied to EM grids and stained with 4% uranyl acetate: A) GII.10 VLPs untreated, B) GII.10 VLPs pretreated with 5B18 IgG, C) GII.10 VLPs pretreated with Nano-85, and D) GII.10 VLPs pretreated with Nano-25.

FIG. 5: Electron microscopy of GII.4 norovirus virus-like particles pretreated at an approx. 1:1 molar ratio with Nano-85; samples were applied to EM grids and stained with 4% uranyl acetate: A) GII.4 VLPs untreated, B) GII.4 VLPs pretreated with Nano-85.

FIG. 6: Inhibition of binding to porcine gastric mucin (PGM) by antibodies of the invention. GII.10 VLPs A) or GII.4 VLPs B) were pre-incubated with serially diluted Nano-85 and added to plates coated with PGM. The bound VLPs were detected with polyclonal antibody to GII.10 or GII.4 VLPs. The percentage (%) inhibition was calculated by dividing the OD490 of VLP-Nanobody complex by the average OD490 of VLPs alone, which was set to 100% binding. X-axis: nanobody concentration (μg/ml), Y-axis: % inhibition.

Figure 7:
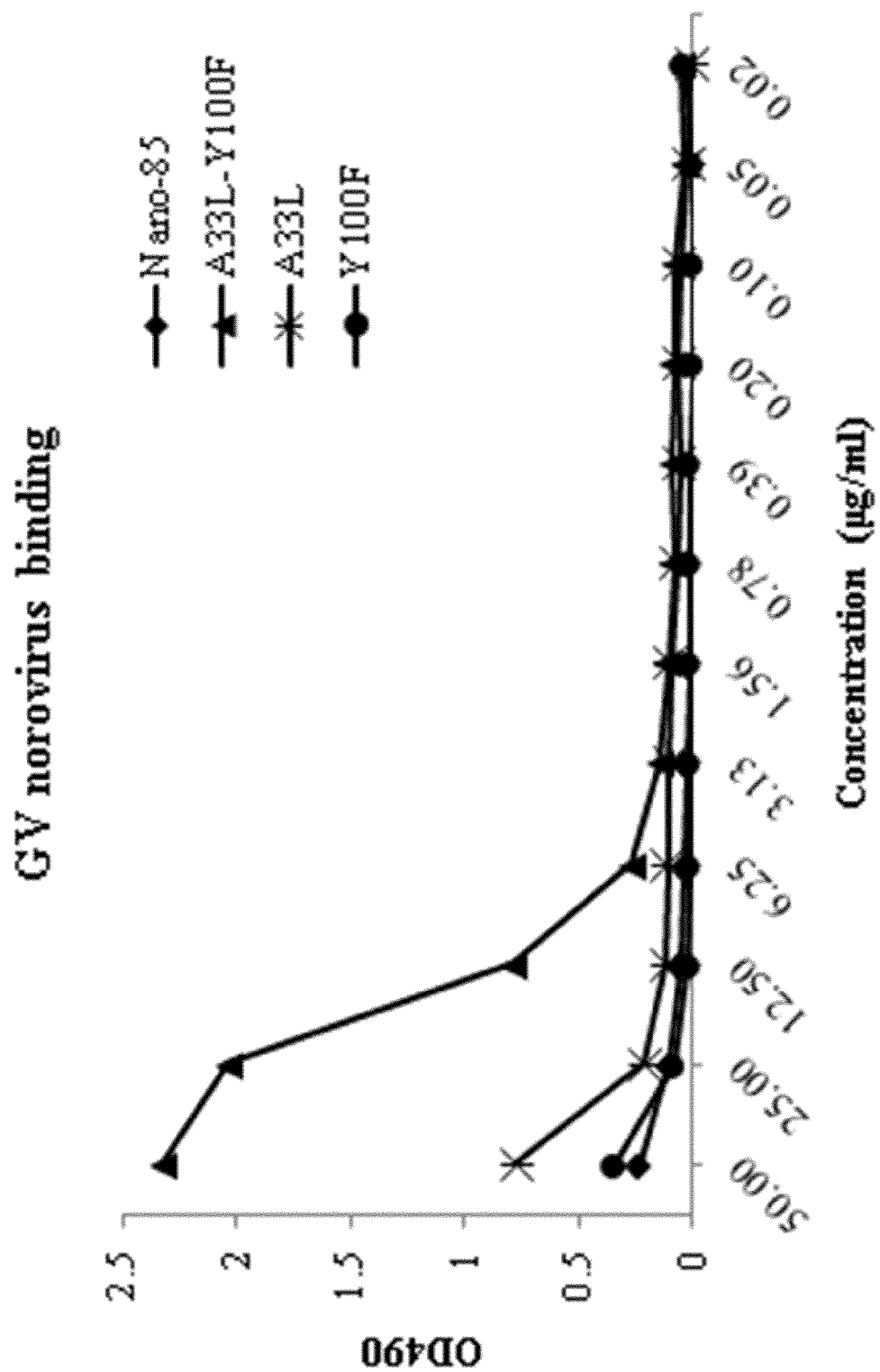

FIG. 7: Improved binding of Nano-85 muteins to genogroup V norovirus. Experimental conditions were as described for FIG. 1A; X-axis: nanobody concentration (μg/ml), Y-axis: Absorption at 490 nm.

Figure 8:
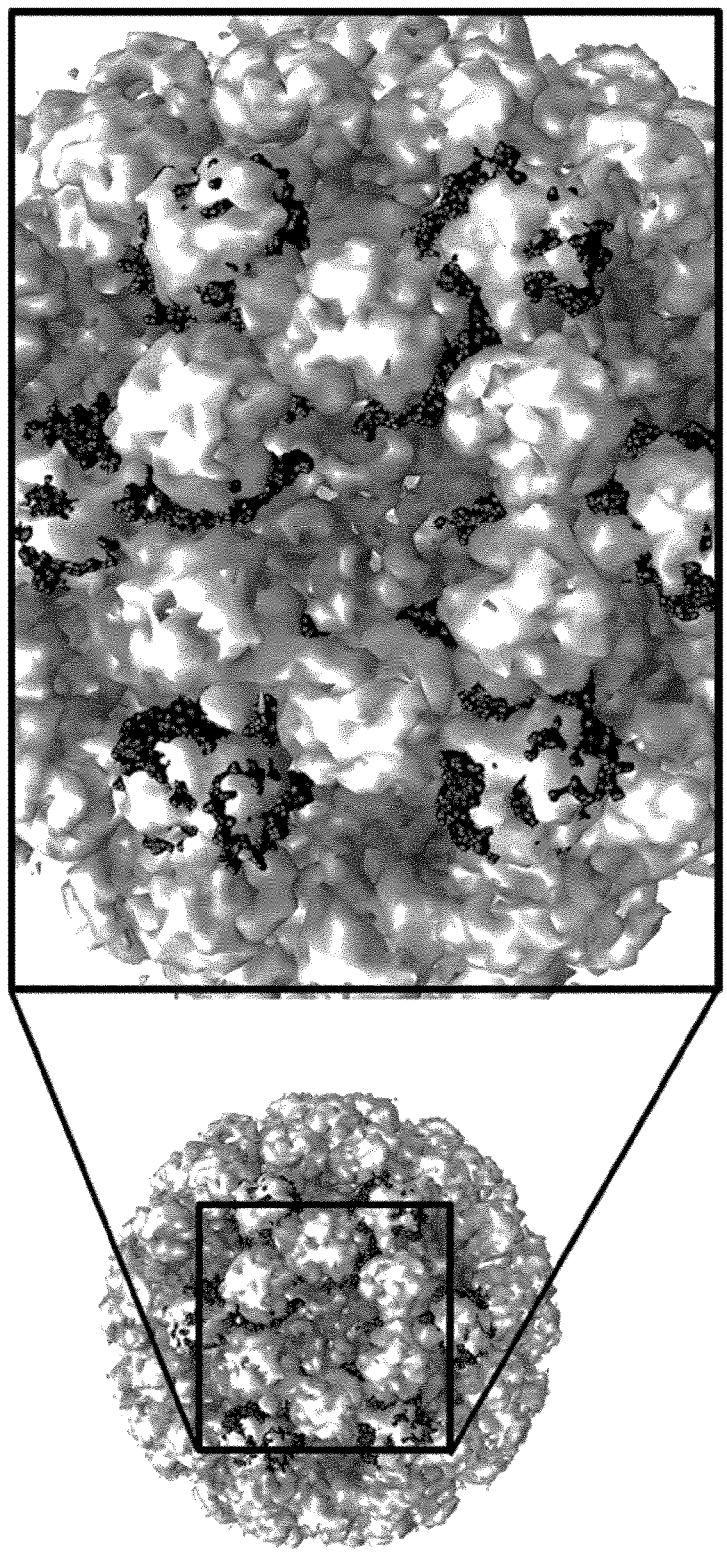

FIG. 8: Superposition of Nano-85 onto the cryo-EM structure of GII.10 VLP. Six Nano-85-P domain (black spheres) complexes were positioned onto the VLP (light grey) in order to show the possible clashes in the two-fold axes. The space available suggests Nano-85 is able to bind at all possible P dimers simultaneously.

EXAMPLES

Example 1: Materials and Methods

VLP Production

The capsid gene of Norovirus GII.10 Vietnam026 (AF504671), GII.12 Hiro (AB044366), GI.1 Norwalk virus (AY502016), and GII.4 NSW-2012 (AFV08795) was cloned into a baculovirus expression system as previously described (Hansman, G. S., L. T. Doan, T. A. Kguyen, S. Okitsu, K. Katayama, S. Ogawa, K. Natori, N. Takeda, Y. Kato, O. Nishio, M. Noda, and H. Ushijima. 2004. Detection of norovirus and sapovirus infection among children with gastroenteritis in Ho Chi Minh City, Vietnam. Arch Virol 149:1673-1688; Lin, C. M., F. M. Wu, H. K. Kim, M. P. Doyle, B. S. Michael, and L. K. Williams. 2003. A comparison of hand washing techniques to remove *Escherichia coli* and caliciviruses under natural or artificial fingernails. J Food Prot 66:2296-2301). VLPs were harvested at five days post infection. The supernatant was pelletized and applied to a 15-45% sucrose ultracentrifugation gradient (Beckmann SW40-Ti rotor) for 2 h at 4° C. Fractions were confirmed using EM and homogenous particles were pooled and concentrated to 2-10 mg/ml.

P Domain Production

The P domain of GII.10 (Vietnam026), GII.12 (Hiro), GII.4 (Saga-2006), and GII.4 (NSW-2012) was produced as previously described (Hansman, G. S., C. Biertumpfel, I. Georgiev, J. S. McLellan, L. Chen, T. Zhou, K. Katayama, and P. D. Kwong. 2011. Crystal structures of GII.10 and GII.12 norovirus protruding domains in complex with histo-blood group antigens reveal details for a potential site of vulnerability. Journal of virology 85:6687-6701). Briefly, the P domain was cloned in expression vector pMal-c2X (New England Biolabs) and transformed into BL21 cells. Transformed cells were grown at 37° C. in LB medium for 2 h. Expression was induced with IPTG (0.75 mM) at $OD_{600}$ of 0.6 for 18 h at 22° C. Cells were harvested by centrifugation and disrupted by sonication. A His-tagged fusion-P domain protein was purified from a Ni-NTA column and digested with HRV-3C protease (Novagen) overnight at 4° C. The cleaved P domain was separated on the Ni-NTA column and dialyzed in gel filtration buffer (GFB, 0.35 M NaCl and 2.5 mM Tris (pH 7.4)) overnight at 4° C. The P domain was further purified by size exclusion chromatography with a Superdex-200 column and stored in GFB at 4° C.

Nanobody Production

A single alpaca was injected subcutaneously on days 0, 7, 14, 21, 28 and 35 with ~115 μg GII.10 VLP protein per injection (VIB Nanobody Service Facility, at Vrije University Brussel, Belgium). A VHH library was constructed and screened for the presence of antigen-specific nanobodies. A VHH library of about $10^8$ independent transformants was obtained. Three consecutive rounds of panning were performed on solid-phase coated with GII.10 VLPs (20 μg/well). Totally, 143 individual colonies were randomly selected. Crude periplasmic extracts were analyzed using ELISA for the presence of antigen specific Nanobodies. Forty-seven colonies were positive and nucleotide sequencing revealed these represented 35 different Nanobodies that belonged to 17 distinct groups based on sequence alignments. In this study, Nano-85 was examined.

Expression and Purification of Nanobody Proteins.

The Nanobodies were cloned into a pHEN6C expression vector and grown in E. coli WK6 cells overnight at 28° C. Expression was induced with 1 mM IPTG at $OD_{600}$=0.7. Nanobodies were extracted from periplasm and the supernatant collected. Nanobodies were separated on a Ni-NTA column and purified by size exclusion chromatography using a Superdex-200 column as previously described (9). Nanobodies were concentrated to 2-5 mg/ml and stored in GFB.

ELISA Experiments

Nanobody reactivity against VLPs and P domains were measured using a direct ELISA as previously described (Hansman, G. S., R. Guntapong, Y. Pongsuwanna, K. Natori, K. Katayama, and N. Takeda. 2006. Development of an antigen ELISA to detect sapovirus in clinical stool specimens. Arch Virol 151:551-561). Briefly, microtiter plates were coated with 2 μg/ml of VLPs (GII.10, GII.12, and GII.4) or 7 μg/ml GII.10 P domain. VLPs were diluted in PBS (pH 7.4), which preserved their structural integrity (Hansman, G. S., D. W. Taylor, J. S. McLellan, T. J. Smith, I. Georgiev, J. R. Tame, S. Y. Park, M. Yamazaki, F. Gondaira, M. Miki, K. Katayama, K. Murata, and P. D. Kwong. 2012. Structural basis for broad detection of genogroup II noroviruses by a monoclonal antibody that binds to a site occluded in the viral particle. Journal of virology 86:3635-3646). Nanobodies were serially diluted in PBS from a starting concentration of ~10 μM, and then 100 μl was added to triplicate wells. The His-tagged-Nanobodies were detected with a secondary HRP-conjugated anti-His IgG. For sandwich ELISA, plates were coated overnight with commercially produced monoclonal antibodies (ViroStat, USA). VLPs (GII.10, GII.12, GII.4, and GI.1) were added for 1 h at 37° C., and then detected as described above. Detection of norovirus virions from clinical specimens was also performed using the sandwich ELISA with ~1 μM GII.4 specific monoclonal antibody as capture and ~1 μM Nano-85 as detector. A detection limit was set at 0.15 for all experiments, which was ~3 times the value of the (PBS only) negative control.

Purification and Crystallization of Norovirus P Domain and Nanobody Complexes

The P domain and Nanobody were mixed in a 1:1.4 molar ratio and incubated at 25° C. for ~90 min. The complex was purified by size exclusion chromatography using a Superdex-200 column and concentrated to 2.8 mg/ml. Complex crystals were grown using hanging-drop vapor diffusion method at 18° C. GII.10 P domain and Nano-85 crystals were grown in 0.2 M calcium acetate, 18% (w/v), PEG8000, and 0.1 M sodium cacodylate (pH 6.5); GII.10 P domain and Nano-25 crystals were grown in 20% (w/v) PEG3350, and 0.2 M ammonium dihydrogen phosphate; Saga-2006 GII.4 P domain and Nano-85 crystals were grown in 10% (w/v) PEG8000 and 0.1 M HEPES (pH 7.5); and NSW-2012 GII.4 P domain and Nano-85 crystals were grown in 10% (w/v) PEG8000 and 0.1 M HEPES (pH 7.5). Prior to flash-freezing in liquid nitrogen, crystals were transferred to a cryoprotectant containing the mother liquor in 30% ethylene glycol.

Data Collection, Structure Solution, and Refinement

X-ray diffraction data were collected at the European Synchrotron Radiation Facility, France at beamlines BM30A and ID23-1 and processed with XDS (Kabsch, W. 1993. Automatic processing of rotation diffraction data from crystals of initially unknown symmetry and cell constants. J Appl Cryst 26:795-800). Structures were solved by molecular replacement in PHASER (McCoy, A. J., R. W. Grosse-Kunstleve, P. D. Adams, M. D. Winn, L. C. Storoni, and R. J. Read. 2007. Phaser crystallographic software. Journal of Applied Crystallography 40:658-674). The GII.10 P domain was solved using molecular replacement with GII.10 P domain (PDB ID 3ONU) and a previously determined Nanobody (PDB ID 3P0G) as search models. Structures were refined in multiple rounds of manual model building in COOT (Emsley, P., B. Lohkamp, W. G. Scott, and K. Cowtan. 2010. Features and development of Coot. Acta Crystallogr D Biol Crystallogr 66:486-501) and refined with PHENIX (Adams, P. D., P. V. Afonine, G. Bunkóczi, V. B. Chen, I. W. Davis, N. Echols, J. J. Headd, L.-W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. 2010. PHENIX: a comprehensive Python-based system for macromolecular structure solution. Acta Crystallogr D Biol Crystallogr 66:213-221) Structures were validated with Procheck (Morris, A. L., M. W. MacArthur, E. G. Hutchinson, and J. M. Thornton. 1992. Stereochemical quality of protein structure coordinates. Proteins 12:345-364) and MolProbity (Chen, V. B., W. B. Arendall, 3rd, J. J. Headd, D. A. Keedy, R. M. Immormino, G. J. Kapral, L. W. Murray, J. S. Richardson, and D. C. Richardson. 2010. MolProbity: all-

Example 2

Nanobody Binding Specificity

Nano-85 was analyzed in this study. Initially, the Nanobody binding characteristics were analyzed with GII.10 VLPs and the corresponding P domain (FIG. 1A). Nano-85 detected GII.10 VLPs at a dilution of 64,000 (~170 pM). A similar binding pattern was also observed with GII.10 P domains, where Nano-85 detected the P domains at dilutions of 17,800. The cross-reactivities of the Nanobody were analyzed using VLPs from other genotypes (GI.1, GII.4 (NSW-2012), and GII.12). Nano-85 detected GII.4 and GII.12 VLPs at a dilution of 32,000 (~340 pM) and GI.1 VLPs at a lower dilution of 4,000 (FIG. 1A).

Figure 1B:
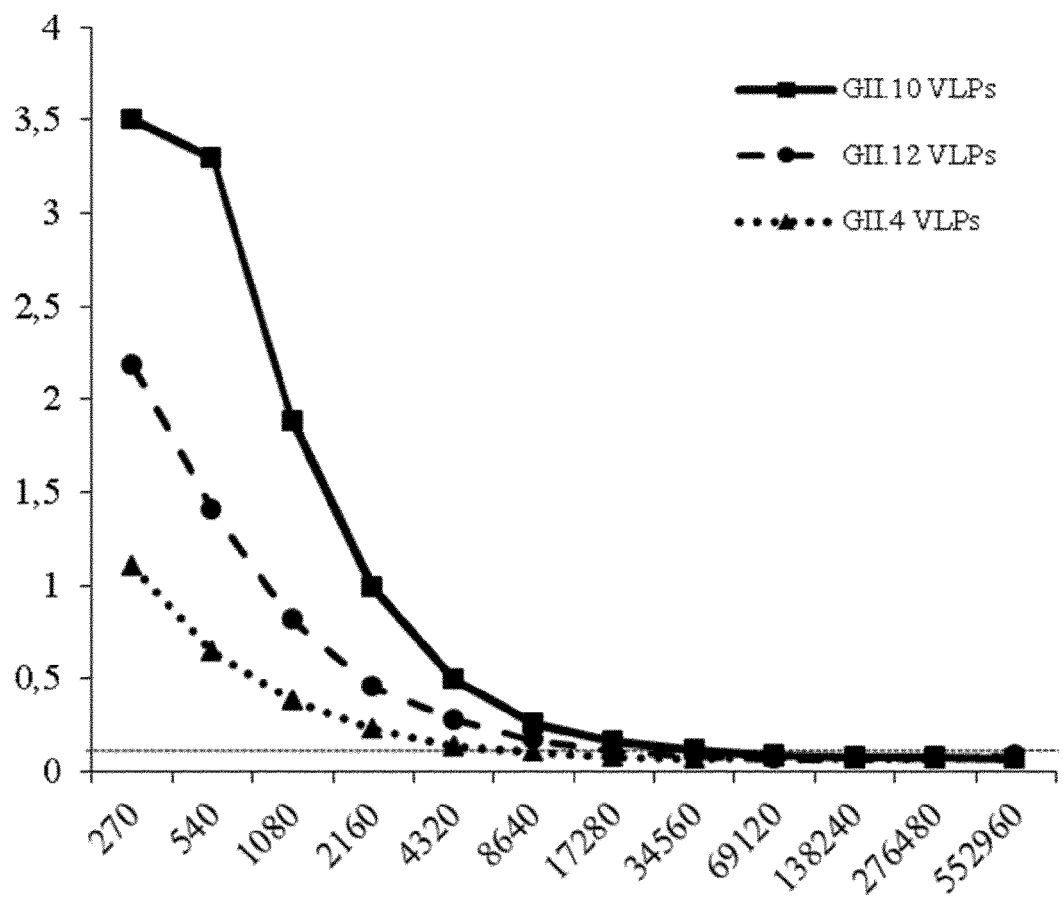

A sandwich ELISA was performed to confirm the binding of Nano-85 to intact particles. Wells were first coated with GII genotype specific monoclonal antibodies and then GII.10, GII.12, and GII.4 (NSW-2012) VLPs were added. Nano-85 detected the captured GII.10, GII.12, and GII.4 VLPs at dilutions of 17,280, 8,640, and 2,160, respectively (FIG. 1B). Twelve GII.4 positive clinical stool specimens were also tested in order to determine the Nanobody diagnostic potential. Nano-85 was able to detect 8 of 12 norovirus GII.4 positive specimens (Table 1). No cross-reactivities were observed with RT-PCR negative control specimens.

TABLE 1

Detection of norovirus in stool samples

| Sample | | | | | | | |
|---|---|---|---|---|---|---|---|
| 8 | 17 | 19 | 42 | 47 | 49 | 58 | 59 |

| $OD_{490}$ | 0.11 | 0.16 | 0.20 | 0.14 | 0.14 | 0.12 | 0.23 | 0.12 |

The Nanobody tightly bound to all three P domains with Kds ~3 to 30 nM.

X-Ray Structures of P Domain and Nanobody Complexes

In order to identify the Nanobody recognition sites, we determined the X-ray crystal structures of GII.10 P domain in complex with Nano-25 and Nano-85. We also determined the X-ray crystal structures of GII.4 (Saga-2006) P domain Nano-85 complex and GII.4 (NSW-2012) P domain Nano-85 complex in order to better understand cross-reactivity binding interactions at the atomic level. The GII.10 P1 subdomain comprised of residues 222-277 and 427-549, whereas the P2 subdomain was located between residues 278-426 (Hansman, G. S., C. Biertumpfel, I. Georgiev, J. S. McLellan, L. Chen, T. Zhou, K. Katayama, and P. D. Kwong. 2011. Crystal structures of GII.10 and GII.12 norovirus protruding domains in complex with histo-blood group antigens reveal details for a potential site of vulnerability. Journal of virology 85:6687-6701). The GII.4 P1 subdomains comprised of residues 224-274 and 418-530, whereas the P2 subdomains were located between residues 275-417. The P1 subdomains compromised of β-sheets and one α-helix, whereas the P2 subdomains contained six antiparallel β-strands that formed a barrel-like structure. The P domains in the complex structures were reminiscent of the apo structures and showed little conformational change. Nano-85 was well refined for most residues and showed a typical immunoglobulin domain fold of other known Nanobody structures (Aline Desmyter, T. R. T., Mehdi Arbabi Ghahroudi, Minh-Hoa Dao Thi, Freddy Poortmans, Raymond Hamers, Serge Muyldermans & Lode Wyns. 1996. Crystal structure of a camel single-domain VH antibody fragment in complex with lysozyme. Nature structural biology 3:803-81). As expected, amino acid changes were mostly located in CDR1, CDR2, and CDR3. Nano-85 CDR3 contained a seven amino acid insertion.

Structure of GII.10 P Domain and Nano-85 Complex

Nano-85 bound with a monomeric interaction at the lower section of the GII.10 P1 subdomain (FIG. 2). The total interface surface area of the GII.10 P domain and Nano-85 was 736 A2 as calculated using PISA software (Krissinel, E., and K. Henrick. 2007. Inference of macromolecular assemblies from crystalline state. Journal of molecular biology 372:774-797). Crystal packing showed alternative binding sites on the GII.10 P domain, however these were less favorable, having an interface surface area less than 360 Å2 and only a few hydrogen bonds. The Nano-85 was held with a network of binding interactions, including hydrogen bonds and hydrophobic interactions. Eight GII.10 P domain residues (Trp528, Asn50, Thr534, Trp528, Leu477, Phe532, and Tyr533) formed direct hydrogen bonds with Nano-85. Four GII.10 P domain residues (Leu477, Phe525, Val529, and Phe532) were formed hydrophobic interactions with Nano-85. One electrostatic interaction was observed between Phe532 of GII.10 P domain and Lys96 of Nano-85.

Structure of GII.4 P Domains and Nano-85 Complexes

In order to describe Nano-85 binding interactions with other noroviruses, we solved the X-ray crystal structures of two different GII.4 P domains (Saga-2006 and NSW-2012) in complex with Nano-85. Saga-2006 and NSW-2012 P domains had 93% amino acid identity and both had ~55% amino acid identity with GII.10 P domain. Similar to GII.10, Nano-85 bound at the lower section of the GII.4 P1 subdomain. The total interface surface area of the GII.4 P domains and Nano-85 were ~736 Å$^2$. Nano-85 was held with a network of binding interactions similar to GII.10 P domain. Eight GII.4 P domain residues (Trp528, Asn50, Thr534, Trp528, Leu477, Phe532, and Tyr533) formed direct hydrogen bonds with Nano-85. Four GII.4 P domain residues (Leu477, Phe525, Val529, and Phe532) formed hydrophobic interactions with Nano-85. One electrostatic interaction was observed between Phe532 of GII.4 P domain and Lys96 of Nano-85.

Conservation of Nanobody Binding Sites

The norovirus P domain amino acid sequences of representative GII genotypes was aligned using ClustalX. Six of eight GII P domain residues interacting with Nano-85 were highly conserved among the diverse genotypes: The sequence was WVNQFYT (SEQ ID NO:10) for GII.10, GII.6, and GII.4; WVNQFYS (SEQ ID NO:11) for GII.1, GII.2, GII.5, GII.7, GII.8, and GII.12; WVNPFYT (SEQ ID NO:12) for GII.3. Interestingly, the member of genogroup I included in this study only has four amino acids of the motifs in common with the members of GII (amino acids WV and FY) and is recognized anyway (FIG. 1A).

Superposition of the GII.10 P Domain Nanobody Complex on the GII.10 VLP

The binding sites of the Nanobodies were located in the lower region of the P domain. Superposition of the X-ray crystal structure of GII.10 P domain Nanobody complexes on the cryo-EM GII.10 VLP showed a discernible Nanobody clash on the particle. Likewise, the X-ray crystal structure of the GII.10 P domain Fab complex showed a similar clash on the cryo-EM GII.10 VLP. Nanobody and Fab binding to the norovirus P domains does not cause any conformational changes in the P domain. However, the hinge region between the S and P domains is expected to allow a certain degree of flexibility of the P domains so that the Nanobody can attach to the occluded site on the particles (Smith, T. J. 2011. Structural studies on antibody recognition and neutralization of viruses. Curr Opin Virol 1:150-156). As shown in FIG. 8, Nano-85 can occupy all possible P dimers simultaneously.

Example 3: Disassembly of Norovirus VLPs by Nano-85

GII.10 VLPs (FIG. 4) were incubated with the following antibodies: control (no antibody) (FIG. 4A); monoclonal 5B18 IgG (as disclosed in EP 2 757 111 A1, FIG. 4 B), Nano-85 (FIG. 4 C), and Nano-25 (FIG. 4 D). Nano-25 is a nanobody binding to a similar site of the norovirus VLP, but contacting different amino acids of the viral capsid. As shown in FIG. 4, only Nano-85 causes disassembly of the VLPs. FIG. 5 shows results of the analogous experiment using GII.4 VLPs.

Example 4: Inhibition of Norovirus Binding to Porcine Gastric Mucin (PGM) by Nano-85

Histo-blood group antigens (HBGAs) were found to be the natural binding factor on the cell for noroviruses (Tan et al. (2005), Trends in Microbiology 13(6):285). Moreover, it was found that porcine gastric mucin (PGM) competes with HBGA in binding to norovirus (Tian et al. (2005), Lett Appl Microbiol 41(4):315), which is why binding of norovirus to PGM has been used as a model system for binding of noroviruses to their natural binding factors. Accordingly, binding of norovirus GII.10 and GII.4 VLPs to PGM was determined after preincubation of the VLPs with serial dilutions of Nano-85. As shown in FIG. 6, Nano-85 inhibits norovirus binding to PGM in a concentration-dependent manner, with half-maximal inhibition occurring at a concentration of less than 10 µg/ml.

Example 5: Redesign of Nano-85

The information underlying FIG. 2 was used to increase binding of Nano-85 to genogroup V (GV) norovirus by modifying Nano-85 CDR regions. Residues A33 and Y100, known to be involved in binding to GII norovirus, were modified to better fit into the binding site of genogroup V norovirus. The binding site on the P domain is unchanged. As shown in FIG. 7, a double A33L/Y100F mutein of Nano-85 shows strongly increased binding to genogroup V norovirus.

The invention claimed is:

1. A single-domain antibody (VHH) binding specifically to the amino acid sequence W-V-N-X$^1$-F-Y-X$^2$ (SEQ ID NO:1), wherein:
   (a) X$^1$ represents any amino acid, preferably Q or P, and
   (b) X$^2$ represents any amino acid, preferably, T or S, in a norovirus polypeptide;
   wherein the single-domain antibody comprises the complementarity determining regions (CDRs) (i) CDR1: GSIFSIYA (SEQ ID NO:6) or GSIFSIYL (SEQ ID NO: 13), (ii) CDR2: ISSGGGTN (SEQ ID NO:7), and (iii) CDR3: KREDYSAYAPPSGS (SEQ ID NO:8) or KREDFSAYAPPSGS (SEQ ID NO: 14).

2. The single-domain antibody of claim 1, wherein the single-domain antibody specifically binds to a sequence selected from:

(i)
(SEQ ID NO: 2)
F-X$^6$-X$^5$-X$^4$-X$^3$-W-V-N-X$^1$-F-Y-X$^2$;

(ii)
(SEQ ID NO: 3)
X$^{53}$X$^{52}$ ... X$^3$-W-V-N-X$^1$-F-Y-X$^2$;
and/or (iii)
(SEQ ID NO: 4)
X$^{53}$X$^{52}$ ... X$^8$-F-X$^6$-X$^5$-X$^4$-X$^3$-W-V-N-X$^1$-F-Y-X$^2$, wherein X$^3$ to X$^{52}$ represent any amino acid and wherein X$^{53}$ represents a non-charged amino acid, preferably, L, P, M, Q, or N.

3. The single-domain antibody of claim 1, wherein the single chain antibody is a VHH encoded by a nucleotide sequence having at least 70% sequence identity to SEQ ID NO:5.

4. The single-domain antibody of claim 1, wherein the single-domain antibody comprises the complementarity determining regions (CDRs) (i) CDR1: GSIFSIYA (SEQ ID NO:6), (ii) CDR2: ISSGGGTN (SEQ ID NO:7), and (iii) CDR3: KREDYSAYAPPSGS (SEQ ID NO:8).

5. The single-domain antibody claim 1, wherein the single-domain antibody comprises the amino acid sequence of SEQ ID NO:9.

6. The single-domain antibody of claim 1, wherein the norovirus polypeptide is a norovirus capsid polypeptide.

7. A host cell comprising the single-domain antibody according to claim 1.

8. A kit for diagnosing, preventing or/and treating a norovirus infection, comprising the single-domain antibody of claim 1 in a housing.

9. The single domain antibody of claim 1, wherein the single-domain antibody comprises an amino acid sequence having 80% sequence identity to SEQ ID NO:9.

10. The single-domain antibody claim 1, wherein the single-domain antibody comprises the amino acid sequence of SEQ ID NO:9 with one or more amino acid substitutions selected from the group consisting of A33L, Y100F, and A33L/Y100F.

* * * * *

SEQUENCE LISTING

```
<160> NUMBER OF SEQ ID NOS: 15

<210> SEQ ID NO 1
<211> LENGTH: 7
<212> TYPE: PRT
<213> ORGANISM: Norovirus sp.
<220> FEATURE:
<221> NAME/KEY: MOD_RES
<222> LOCATION: (4)..(4)
<223> OTHER INFORMATION: Any amino acid, preferably Q or P
<220> FEATURE:
<221> NAME/KEY: MOD_RES
<222> LOCATION: (7)..(7)
<223> OTHER INFORMATION: Any amino acid, preferably T or S

<400> SEQUENCE: 1

Trp Val Asn Xaa Phe Tyr Xaa
1               5

<210> SEQ ID NO 2
<211> LENGTH: 12
<212> TYPE: PRT
<213> ORGANISM: Norovirus sp.
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid, preferably Q or P
<220> FEATURE:
<221> NAME/KEY: MOD_RES
<222> LOCATION: (12)..(12)
<223> OTHER INFORMATION: Any amino acid, preferably T or S

<400> SEQUENCE: 2

Phe Xaa Xaa Xaa Xaa Trp Val Asn Xaa Phe Tyr Xaa
1               5                   10

<210> SEQ ID NO 3
<211> LENGTH: 58
```

-continued

```
<212> TYPE: PRT
<213> ORGANISM: Norovirus sp.
<220> FEATURE:
<221> NAME/KEY: MOD_RES
<222> LOCATION: (1)..(1)
<223> OTHER INFORMATION: A non-charged amino acid, preferably L, P, M,
      Q, or N
<220> FEATURE:
<221> NAME/KEY: MOD_RES
<222> LOCATION: (2)..(51)
<223> OTHER INFORMATION: Any amino acid
<220> FEATURE:
<221> NAME/KEY: MOD_RES
<222> LOCATION: (55)..(55)
<223> OTHER INFORMATION: Any amino acid, preferably Q or P
<220> FEATURE:
<221> NAME/KEY: MOD_RES
<222> LOCATION: (58)..(58)
<223> OTHER INFORMATION: Any amino acid, preferably, T or S

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Trp Val Asn Xaa Phe Tyr Xaa
    50                  55

<210> SEQ ID NO 4
<211> LENGTH: 59
<212> TYPE: PRT
<213> ORGANISM: Norovirus sp.
<220> FEATURE:
<221> NAME/KEY: MOD_RES
<222> LOCATION: (1)..(1)
<223> OTHER INFORMATION: A non-charged amino acid, preferably L, P, M,
      Q, or N
<220> FEATURE:
<221> NAME/KEY: MOD_RES
<222> LOCATION: (2)..(47)
<223> OTHER INFORMATION: Any amino acid
<220> FEATURE:
<221> NAME/KEY: MOD_RES
<222> LOCATION: (49)..(52)
<223> OTHER INFORMATION: Any amino acid
<220> FEATURE:
<221> NAME/KEY: MOD_RES
<222> LOCATION: (56)..(56)
<223> OTHER INFORMATION: Any amino acid, preferably Q or P
<220> FEATURE:
<221> NAME/KEY: MOD_RES
<222> LOCATION: (59)..(59)
<223> OTHER INFORMATION: Any amino acid, preferably, T or S

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Phe
        35                  40                  45

Xaa Xaa Xaa Xaa Trp Val Asn Xaa Phe Tyr Xaa
        50                  55

<210> SEQ ID NO 5
<211> LENGTH: 381
<212> TYPE: DNA
```

```
<213> ORGANISM: Artificial Sequence
<220> FEATURE:
<223> OTHER INFORMATION: Description of Artificial Sequence: Synthetic
      sb-AB from Lama pacos

<400> SEQUENCE: 5
gatgtgcagc tggtggagtc tgggggaggc ttggtgcagc ctgggggtc tctgagactc        60 tcctgtgcag cctctggaag catcttcagt atctatgcca tgggctggta ccgccaggct       120
ccagggaagc agcgcgagtt ggtcgcttct attagtagtg gtggtggcac aaactatgca       180
gactccgtga agggccgatt caccatctcc ggagacaacg ccaagaacac ggtgtatctg       240
caaatgaaca gcctgaaacc tgaggacacg gccgtctatt actgtaaaag agaagactat       300
agcgcctatg cgcccccgag tggttccgg ggccggggga cccaggtcac cgtctcctca       360
caccaccatc accatcacta a                                                 381

<210> SEQ ID NO 6
<211> LENGTH: 8
<212> TYPE: PRT
<213> ORGANISM: Lama pacos

<400> SEQUENCE: 6

Gly Ser Ile Phe Ser Ile Tyr Ala
1               5

<210> SEQ ID NO 7
<211> LENGTH: 8
<212> TYPE: PRT
<213> ORGANISM: Lama pacos

<400> SEQUENCE: 7

Ile Ser Ser Gly Gly Gly Thr Asn
1               5

<210> SEQ ID NO 8
<211> LENGTH: 14
<212> TYPE: PRT
<213> ORGANISM: Lama pacos

<400> SEQUENCE: 8

Lys Arg Glu Asp Tyr Ser Ala Tyr Ala Pro Pro Ser Gly Ser
1               5                   10

<210> SEQ ID NO 9
<211> LENGTH: 135
<212> TYPE: PRT
<213> ORGANISM: Artificial Sequence
<220> FEATURE:
<223> OTHER INFORMATION: Description of Artificial Sequence: Synthetic
      sb-AB from Lama pacos

<400> SEQUENCE: 9

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Tyr
            20                  25                  30

Ala Met Gly Trp Tyr Arg Gln Ala Pro Gly Lys Gln Arg Glu Leu Val
        35                  40                  45

Ala Ser Ile Ser Ser Gly Gly Gly Thr Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80
```

-continued

```
Gln Met Asn Ser Leu Lys Pro Glu Asp Thr Ala Val Tyr Tyr Cys Lys
                 85                  90                  95

Arg Glu Asp Tyr Ser Ala Tyr Ala Pro Pro Ser Gly Ser Arg Gly Arg
            100                 105                 110

Gly Thr Gln Val Thr Val Ser Ser Gly Arg Tyr Pro Tyr Asp Val Pro
        115                 120                 125

Asp Tyr Gly Ser Gly Arg Ala
    130             135

<210> SEQ ID NO 10
<211> LENGTH: 7
<212> TYPE: PRT
<213> ORGANISM: Norovirus sp.

<400> SEQUENCE: 10

Trp Val Asn Gln Phe Tyr Thr
1               5

<210> SEQ ID NO 11
<211> LENGTH: 7
<212> TYPE: PRT
<213> ORGANISM: Norovirus sp.

<400> SEQUENCE: 11

Trp Val Asn Gln Phe Tyr Ser
1               5

<210> SEQ ID NO 12
<211> LENGTH: 7
<212> TYPE: PRT
<213> ORGANISM: Norovirus sp.

<400> SEQUENCE: 12

Trp Val Asn Pro Phe Tyr Thr
1               5

<210> SEQ ID NO 13
<211> LENGTH: 8
<212> TYPE: PRT
<213> ORGANISM: Lama pacos

<400> SEQUENCE: 13

Gly Ser Ile Phe Ser Ile Tyr Leu
1               5

<210> SEQ ID NO 14
<211> LENGTH: 14
<212> TYPE: PRT
<213> ORGANISM: Lama pacos

<400> SEQUENCE: 14

Lys Arg Glu Asp Phe Ser Ala Tyr Ala Pro Pro Ser Gly Ser
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 15

His His His His His His
1               5
```